US010463710B2

(12) United States Patent
Tsao et al.

(10) Patent No.: US 10,463,710 B2
(45) Date of Patent: Nov. 5, 2019

(54) SHORT SYNTHETIC PEPTIDE FOR THE TREATMENT AND/OR PROPHYLAXIS OF AUTOIMMUNE AND INFLAMMATORY DISORDERS

(71) Applicants: MacKay Memorial Hospital, Taipei (TW); Yeou-Ping Tsao, Taipei (TW); Tsung-Chuan Ho, Taipei (TW)

(72) Inventors: Yeou-Ping Tsao, Taipei (TW); Tsung-Chuan Ho, Taipei (TW)

(73) Assignee: MacKay Memorial Hospital, Taipei (TW)

( * ) Notice: Subject to any disclaimer, the term of this patent is extended or adjusted under 35 U.S.C. 154(b) by 0 days.

(21) Appl. No.: 15/569,142

(22) PCT Filed: Apr. 14, 2016

(86) PCT No.: PCT/CN2016/079284
§ 371 (c)(1),
(2) Date: Oct. 25, 2017

(87) PCT Pub. No.: WO2016/173401
PCT Pub. Date: Nov. 3, 2016

(65) Prior Publication Data
US 2018/0140656 A1 May 24, 2018

Related U.S. Application Data

(60) Provisional application No. 62/152,980, filed on Apr. 27, 2015.

(51) Int. Cl.
| | |
|---|---|
| A61K 38/08 | (2019.01) |
| C07K 7/06 | (2006.01) |
| C07K 14/00 | (2006.01) |
| A61P 7/06 | (2006.01) |
| A61P 17/10 | (2006.01) |
| A61P 27/02 | (2006.01) |
| A61P 17/06 | (2006.01) |
| A61P 21/00 | (2006.01) |
| A61P 21/04 | (2006.01) |
| A61P 19/06 | (2006.01) |
| A61P 25/28 | (2006.01) |
| A61P 1/16 | (2006.01) |
| A61P 11/06 | (2006.01) |
| A61P 37/06 | (2006.01) |
| A61P 17/00 | (2006.01) |
| A61P 19/02 | (2006.01) |
| A61P 37/08 | (2006.01) |
| A61P 3/10 | (2006.01) |
| A61P 1/00 | (2006.01) |
| A61P 11/00 | (2006.01) |
| A61P 25/00 | (2006.01) |
| A61P 25/16 | (2006.01) |
| A61P 29/00 | (2006.01) |
| A61P 1/04 | (2006.01) |
| A61P 9/14 | (2006.01) |
| A61K 45/06 | (2006.01) |
| A61P 27/06 | (2006.01) |
| A61P 9/10 | (2006.01) |
| A61P 31/00 | (2006.01) |
| A61P 9/00 | (2006.01) |
| A61P 27/04 | (2006.01) |

(Continued)

(52) U.S. Cl.
CPC .............. *A61K 38/08* (2013.01); *A61K 45/06* (2013.01); *A61P 1/00* (2018.01); *A61P 1/04* (2018.01); *A61P 1/16* (2018.01); *A61P 3/10* (2018.01); *A61P 7/06* (2018.01); *A61P 9/00* (2018.01); *A61P 9/10* (2018.01); *A61P 9/14* (2018.01); *A61P 11/00* (2018.01); *A61P 11/06* (2018.01); *A61P 17/00* (2018.01); *A61P 17/06* (2018.01); *A61P 17/10* (2018.01); *A61P 19/02* (2018.01); *A61P 19/06* (2018.01); *A61P 21/00* (2018.01); *A61P 21/04* (2018.01); *A61P 25/00* (2018.01); *A61P 25/16* (2018.01); *A61P 25/28* (2018.01); *A61P 27/02* (2018.01); *A61P 27/04* (2018.01); *A61P 27/06* (2018.01); *A61P 29/00* (2018.01); *A61P 31/00* (2018.01); *A61P 31/04* (2018.01); *A61P 31/10* (2018.01); *A61P 31/12* (2018.01); *A61P 33/02* (2018.01); *A61P 35/00* (2018.01); *A61P 35/02* (2018.01); *A61P 35/04* (2018.01); *A61P 37/06* (2018.01); *A61P 37/08* (2018.01); *C07K 7/06* (2013.01); *C07K 14/001* (2013.01); *A61K 38/00* (2013.01)

(58) Field of Classification Search
None
See application file for complete search history.

(56) References Cited

U.S. PATENT DOCUMENTS

2010/0041614 A1* 2/2010 Bussolino .............. A61K 49/14
514/1.1

OTHER PUBLICATIONS

Kuek et al.. "Immune-mediated inflammatory diseases (IMIDs) and biologic therapy: a medical revolution", Postgraduate Medical Journal, 2007, pp. 251-260 (Year: 2007).*

(Continued)

*Primary Examiner* — Lianko G Garyu

(57) ABSTRACT

Disclosed herein are synthetic peptides and compositions comprising the same, for the treatment and/or prophylaxis of a disease, disorder and/or a condition related to inflammation. Also disclosed herein are methods of treating and/or preventing a disease, disorder and/or a condition related to inflammation, by administering to a subject in need of such treatment a composition containing a therapeutically effective amount of a synthetic peptide of the present disclosure.

8 Claims, 6 Drawing Sheets

Specification includes a Sequence Listing.

(51) Int. Cl.
*A61P 31/12* (2006.01)
*A61P 35/02* (2006.01)
*A61P 31/04* (2006.01)
*A61P 33/02* (2006.01)
*A61P 35/04* (2006.01)
*A61P 31/10* (2006.01)
*A61P 35/00* (2006.01)
*A61K 38/00* (2006.01)

(56) References Cited

OTHER PUBLICATIONS

National Heart, Lung, and Blood Institute (NHLBI), "So you have Asthma", 2007, pp. 1-49 (Year: 2007).*

* cited by examiner

A

B

SEQUENCE LISTING

```
<160> NUMBER OF SEQ ID NOS: 22

<210> SEQ ID NO 1
<211> LENGTH: 7
<212> TYPE: PRT
<213> ORGANISM: Artificial Sequence
<220> FEATURE:
<221> NAME/KEY: VARIANT
<222> LOCATION: 1
<223> OTHER INFORMATION: Xaa is Ala, Asp, Asn, Leu, Phe or Val
<220> FEATURE:
<223> OTHER INFORMATION: X1X2X3X4X5X6X7
<220> FEATURE:
<221> NAME/KEY: VARIANT
<222> LOCATION: 2
<223> OTHER INFORMATION: Xaa is Ala, Ile, Leu or Val
<220> FEATURE:
<221> NAME/KEY: VARIANT
<222> LOCATION: 3
<223> OTHER INFORMATION: Xaa is Phe, Tyr or Trp
<220> FEATURE:
```

```
<221> NAME/KEY: VARIANT
<222> LOCATION: 4
<223> OTHER INFORMATION: Xaa is Arg or Lys
<220> FEATURE:
<221> NAME/KEY: VARIANT
<222> LOCATION: 5
<223> OTHER INFORMATION: Xaa is Val, Met, Ile, Leu or Gln
<220> FEATURE:
<221> NAME/KEY: VARIANT
<222> LOCATION: 6
<223> OTHER INFORMATION: Xaa is Arg, Gln, Lys or Pro
<220> FEATURE:
<221> NAME/KEY: VARIANT
<222> LOCATION: 7
<223> OTHER INFORMATION: Xaa is Ser or Thr

<400> SEQUENCE: 1

Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: 7-mer

<400> SEQUENCE: 2

Asp Leu Tyr Arg Val Arg Ser
1               5

<210> SEQ ID NO 3
<211> LENGTH: 7
<212> TYPE: PRT
<213> ORGANISM: Artificial Sequence
<220> FEATURE:
<223> OTHER INFORMATION: 7-mer Da

<400> SEQUENCE: 3

Ala Leu Tyr Arg Val Arg Ser
1               5

<210> SEQ ID NO 4
<211> LENGTH: 7
<212> TYPE: PRT
<213> ORGANISM: Artificial Sequence
<220> FEATURE:
<223> OTHER INFORMATION: 7-mer La

<400> SEQUENCE: 4

Asp Ala Tyr Arg Val Arg Ser
1               5

<210> SEQ ID NO 5
<211> LENGTH: 7
<212> TYPE: PRT
<213> ORGANISM: Artificial Sequence
<220> FEATURE:
<223> OTHER INFORMATION: 7-mer Ya

<400> SEQUENCE: 5

Asp Leu Ala Arg Val Arg Ser
1               5

<210> SEQ ID NO 6
<211> LENGTH: 7
<212> TYPE: PRT
<213> ORGANISM: Artificial Sequence
<220> FEATURE:
```

```
<223> OTHER INFORMATION: 7-mer Ra

<400> SEQUENCE: 6

Asp Leu Tyr Ala Val Arg Ser
1               5

<210> SEQ ID NO 7
<211> LENGTH: 7
<212> TYPE: PRT
<213> ORGANISM: Artificial Sequence
<220> FEATURE:
<223> OTHER INFORMATION: 7-mer Va

<400> SEQUENCE: 7

Asp Leu Tyr Arg Ala Arg Ser
1               5

<210> SEQ ID NO 8
<211> LENGTH: 7
<212> TYPE: PRT
<213> ORGANISM: Artificial Sequence
<220> FEATURE:
<223> OTHER INFORMATION: 7-mer R2a

<400> SEQUENCE: 8

Asp Leu Tyr Arg Val Ala Ser
1               5

<210> SEQ ID NO 9
<211> LENGTH: 7
<212> TYPE: PRT
<213> ORGANISM: Artificial Sequence
<220> FEATURE:
<223> OTHER INFORMATION: 7-mer Sa

<400> SEQUENCE: 9

Asp Leu Tyr Arg Val Arg Ala
1               5

<210> SEQ ID NO 10
<211> LENGTH: 7
<212> TYPE: PRT
<213> ORGANISM: Artificial Sequence
<220> FEATURE:
<223> OTHER INFORMATION: 7-mer MK

<400> SEQUENCE: 10

Asp Leu Tyr Arg Met Lys Ser
1               5

<210> SEQ ID NO 11
<211> LENGTH: 7
<212> TYPE: PRT
<213> ORGANISM: Artificial Sequence
<220> FEATURE:
<223> OTHER INFORMATION: 7-mer KP

<400> SEQUENCE: 11

Asp Leu Tyr Lys Val Pro Ser
1               5

<210> SEQ ID NO 12
<211> LENGTH: 7
<212> TYPE: PRT
<213> ORGANISM: Artificial Sequence
<220> FEATURE:
<223> OTHER INFORMATION: 7-mer WI
```

```
<400> SEQUENCE: 12

Asp Leu Trp Arg Ile Arg Ser
1               5

<210> SEQ ID NO 13
<211> LENGTH: 7
<212> TYPE: PRT
<213> ORGANISM: Artificial Sequence
<220> FEATURE:
<223> OTHER INFORMATION: 7-mer IP

<400> SEQUENCE: 13

Asp Ile Tyr Arg Val Pro Ser
1               5

<210> SEQ ID NO 14
<211> LENGTH: 7
<212> TYPE: PRT
<213> ORGANISM: Artificial Sequence
<220> FEATURE:
<223> OTHER INFORMATION: 7-mer NV

<400> SEQUENCE: 14

Asn Val Tyr Arg Val Arg Ser
1               5

<210> SEQ ID NO 15
<211> LENGTH: 7
<212> TYPE: PRT
<213> ORGANISM: Artificial Sequence
<220> FEATURE:
<223> OTHER INFORMATION: 7-mer QK

<400> SEQUENCE: 15

Asp Leu Tyr Arg Gln Lys Ser
1               5

<210> SEQ ID NO 16
<211> LENGTH: 7
<212> TYPE: PRT
<213> ORGANISM: Artificial Sequence
<220> FEATURE:
<223> OTHER INFORMATION: 7-mer VFT

<400> SEQUENCE: 16

Asp Val Phe Arg Val Arg Thr
1               5

<210> SEQ ID NO 17
<211> LENGTH: 7
<212> TYPE: PRT
<213> ORGANISM: Artificial Sequence
<220> FEATURE:
<223> OTHER INFORMATION: 7-mer VL

<400> SEQUENCE: 17

Asp Leu Tyr Arg Leu Arg Ser
1               5

<210> SEQ ID NO 18
<211> LENGTH: 7
<212> TYPE: PRT
<213> ORGANISM: Artificial Sequence
<220> FEATURE:
<223> OTHER INFORMATION: 7-mer R2Q
```

```
<400> SEQUENCE: 18

Asp Leu Tyr Arg Val Gln Ser
1               5

<210> SEQ ID NO 19
<211> LENGTH: 7
<212> TYPE: PRT
<213> ORGANISM: Artificial Sequence
<220> FEATURE:
<223> OTHER INFORMATION: 7-mer DV

<400> SEQUENCE: 19

Val Leu Tyr Arg Val Arg Ser
1               5

<210> SEQ ID NO 20
<211> LENGTH: 7
<212> TYPE: PRT
<213> ORGANISM: Artificial Sequence
<220> FEATURE:
<223> OTHER INFORMATION: 7-mer DF

<400> SEQUENCE: 20

Phe Leu Tyr Arg Val Arg Ser
1               5

<210> SEQ ID NO 21
<211> LENGTH: 7
<212> TYPE: PRT
<213> ORGANISM: Artificial Sequence
<220> FEATURE:
<223> OTHER INFORMATION: 7-mer DL

<400> SEQUENCE: 21

Leu Leu Tyr Arg Val Arg Ser
1               5

<210> SEQ ID NO 22
<211> LENGTH: 6
<212> TYPE: PRT
<213> ORGANISM: Artificial Sequence
<220> FEATURE:
<223> OTHER INFORMATION: 6-mer

<400> SEQUENCE: 22

Asp Leu Tyr Arg Val Arg
1               5
```

SHORT SYNTHETIC PEPTIDE FOR THE TREATMENT AND/OR PROPHYLAXIS OF AUTOIMMUNE AND INFLAMMATORY DISORDERS

CROSS-REFERENCE TO RELATED APPLICATIONS

This application is a national stage of PCT international Application No. PCT/CN2016/079284, filed on Apr. 14, 2016 and published in English on Nov. 3, 2016 with the Publication No. WO2016/173401A1, and claims priority to U.S. Provisional Patent Application No. 62/152,980, filed Apr. 27, 2015, which is incorporated herein by reference in its entirety.

BACKGROUND OF THE INVENTION

1. Field of the Invention

The present disclosure relates to the discovery of a short synthetic peptide, and its use for the treatment and/or prophylaxis of diseases, disorders and/or conditions related to inflammation, such as autoimmune disease and inflammatory disorder.

2. Description of Related Art

Irregular inflammation is a major cause of a wide range of human diseases. A non-limiting list of common medical problems that are directly caused by irregular inflammation include, allergy, allergic conjunctivitis (AC), asthma, psoriasis, rheumatoid arthritis (RA), systemic sclerosis (SSc) and etc. Although there are medicaments available for the treatment of such inflammatory diseases; the results, however, are generally unsatisfactory as evidenced by a lack of efficacy and drug related side effects associated therewith.

Psoriasis

Psoriasis is a chronic skin disorder characterized by cutaneous inflammation, keratinocyte hyperproliferation and desquamation formation, affecting approximately 3% of the general population in the USA. About 40% of the patient are considered to have a moderate to severe form of the disease; and 10-30% of the patients with psoriasis also develop a form of arthritis—psoriatic arthritis, which damages the bone and connective tissue around the joints. Several modalities are currently available for treatment of psoriasis, including topical treatment, phototherapy, and systemic applications (e.g., methotrexate, cyclosporine, or retinoids). However, they are generally considered to be only disease suppressive and disease modifying; none of them are curative. Moreover, many treatments are either cosmetically undesirable, inconvenient for long-term use, or associated with significant toxicity that can result in end-organ damage (such as nephrotoxicity, hypertension, bone marrow toxicity and hepatotoxicity).

Allergic Conjunctivitis (AC)

AC is an inflammation of the conjunctiva resulting from hypersensitivity to one or more allergens. It may be acute, intermittent, or chronic. Also, it is an IgE-mediated inflammatory of conjunctiva. Histamine is the major mediator of the disease, and the histamine-produced allergic reaction may be counteracted by administering anti-histamines, however, use of topical anti-histamines or topical corticosteroids only offers temporarily relief. There remains a need of an is improved agent that may alleviate the symptoms of allergic conjunctivitis.

Allergic Asthma

Allergic asthma is a chronic inflammatory disease of the airways. It is characterized by pulmonary eosinophilia, mucus hypersecretion, an increase in serum levels of allergen-specific IgE, and airway hyper-responsiveness (AHR). Current standard of care (SoC) aims to achieve and maintain asthma control, and includes inhaled corticosteroids (ICS) and long-acting beta-2 agonists (LABAs), alone or in combination. However, more than 50% of the patients failed to achieve control of their asthma with SoC, thereby creating a clear unmet medical need. Further, corticosteroid resistance is a major problem in patients with severe asthma.

Rheumatoid Arthritis (RA)

RA is a systemic autoimmune disease characterized by synovial inflammation and joint destruction. Traditional systemic therapies such as methotrexate, cyclosporine are available for treating RA. In addition, Tofacitinib, a small molecule inhibitor targeting Janus kinase (JAK) contribute to suppress the production of multi-inflammatory cytokines from dendritic cells, Th1 and Th17, and activated B cells. The most commonly observed adverse events associated with Tofacitinib were related to infection, hematologic, hepatic and renal disorders and carcinogenicity. Therefore, there exists a need of new drugs with better efficacy and less adverse effects for treating RA.

Systemic Sclerosis (SSc)

SSc is an autoimmune disease characterized by fibrosis of the skin and internal organs. It is a rare disease with orphan status in the USA. It has a prevalence of 240 cases per million adults, with an annual incidence of 20 cases per million adults. The initiating events leading to SSc remain unknown to this date. The hallmarks of systemic sclerosis are inflammation and autoimmunity, endothelial cell dysfunction leading to widespread vasculopathy, and progressive fibrosis. SSc has a poor prognosis because no therapy has been shown to is reverse or arrest the progression of fibrosis.

Accordingly, there exists a need in the related filed of an improved medication and/or method for the treatment and/or prophylaxis of diseases, disorders, and/or conditions related to inflammation.

SUMMARY OF THE INVENTION

In general, the present disclosure relates to the development of novel compounds and/or methods for treating diseases, disorders or conditions related to inflammation.

Accordingly, the first aspect of the present disclosure aims at providing a short synthetic peptide capable of treating diseases, disorders or conditions related to inflammation. The short synthetic peptide consists of 7 consecutive amino acid residues set forth as $X_1X_2X_3X_4X_5X_6X_7$ (SEQ ID NO: 1), wherein, $X_1$ is alanine (A), aspartic acid (D), asparagine (N), leucine (L), phenylalanine (F), or valine (V);

$X_2$ is alanine (A), isoleucine (I), leucine (L), or valine (V);

$X_3$ is phenylalanine (F), tyrosine (Y) or tryptophan (W);

$X_4$ is arginine (R) or lysine (K);

$X_5$ is valine (V), methionine (M), isoleucine (I), leucine (L), or glutamine (Q);

$X_6$ is arginine (R), glutamine (Q), lysine (K) or proline (P);

$X_7$ is serine (S) or threonine (T); and each $X_2$, $X_3$, $X_4$, $X_6$ and $X_7$ are independently L-form amino acid residues.

According to some preferred embodiments, at least one of $X_1$ and $X_5$ is a D-form amino acid residue, and the synthetic peptide has the amino acid sequence of SEQ ID NO: 2 (hereinafter 7-mer). In one example, $X_1$ is in D-form, such as D-aspartic acid (hereinafter 7-mer DD). In another example, $X_5$ is in D-form, such as D-valine (hereinafter 7-mer DV).

According to other preferred embodiments, the synthetic peptide has the amino acid sequence that is any of SEQ ID NOs: 3, 4, 10, 11, 12, 13, 14, 15, 16, 17, 18, 19, 20 or 21. In one example, the synthetic peptide has the amino acid sequence of SEQ ID NO: 3 (herein after 7-mer Da). In another example, the synthetic peptide has the amino acid sequence of SEQ ID NO: 4 (herein after 7-mer La). In yet another example, the synthetic peptide has the amino acid sequence of SEQ ID NO: 10 (herein after 7-mer MK). In a further example, the synthetic peptide has the amino acid sequence of SEQ ID NO: 11 (herein after 7-mer KP). In still a further example, the synthetic peptide has the amino acid sequence of SEQ ID NO: 12 (herein after 7-mer WI). In yet a further example, the synthetic peptide has the amino acid sequence of SEQ ID NO: 13 (herein after 7-mer IP). In another example, the synthetic peptide has the amino acid sequence of SEQ ID NO: 14 (herein after 7-mer NV). In yet another example, the synthetic peptide has the amino acid sequence of SEQ ID NO: 15 (herein after 7-mer QK). In a further example, the synthetic peptide has the amino acid sequence of SEQ ID NO: 16 (herein after 7-mer VFT). In yet a further example, the synthetic peptide has the amino acid sequence of SEQ ID NO: 17 (herein after 7-mer (V→L)). In still a further example, the synthetic peptide has the amino acid sequence of SEQ ID NO: 18 (herein after 7-mer (R2→Q)). In another example, the synthetic peptide has the amino acid sequence of SEQ ID NO: 19 (herein after 7-mer (D→N)). In other example, the synthetic peptide has the amino acid sequence of SEQ ID NO: 20 (herein after 7-mer (D→F)). In a further example, the synthetic peptide has the amino acid sequence of SEQ ID NO: 21 (herein after 7-mer (D→L)).

The second aspect of the present disclosure aims at providing a medicament and/or a composition suitable for treating diseases, disorders or conditions related to inflammation. The medicament or composition comprises, an effective amount of the synthetic peptide described above, and a pharmaceutically acceptable carrier.

According to some preferred embodiments, at least one of $X_1$, and $X_5$ is a D-form amino acid residue, and the synthetic peptide has the amino acid sequence of SEQ ID NO: 2. In one example, $X_1$ is in D-form, such as D-aspartic acid (hereinafter 7-mer DD). In another example, $X_5$ is in D-form, such as D-valine (hereinafter 7-mer DV).

According to preferred embodiments, the synthetic peptide has the amino acid sequence that is any of SEQ ID NOs: 3, 4, 10, 11, 12, 13, 14, 15, 16, 17, 18, 19, 20, or 21. In one example, the synthetic peptide has the amino acid sequence of SEQ ID NO: 3 (herein after 7-mer Da). In another example, the synthetic peptide has the amino acid sequence of SEQ ID NO: 4 (herein after 7-mer La). In yet another example, the synthetic peptide has the amino acid sequence of SEQ ID NO: 10 (herein after 7-mer MK). In a further example, the synthetic peptide has the amino acid sequence of SEQ ID NO: 11 (herein after 7-mer KP). In still a further example, the synthetic peptide has the amino acid sequence of SEQ ID NO: 12 (herein after 7-mer WI). In yet a further example, the synthetic peptide has the amino acid sequence of SEQ ID NO: 13 (herein after 7-mer IP). In another example, the synthetic peptide has the amino acid sequence of SEQ ID NO: 14 (herein after 7-mer NV). In yet another example, the synthetic peptide has the amino acid sequence of SEQ ID NO: 15 (herein after 7-mer QK). In a further example, the synthetic peptide has the amino acid sequence of SEQ ID NO: 16 (herein after 7-mer VFT). In yet a further example, the synthetic peptide has the amino acid sequence of SEQ ID NO: 17 (herein after 7-mer (V→L)). In still a further example, the synthetic peptide has the amino acid sequence of SEQ ID NO: 18 (herein after 7-mer (R2→Q)). In another example, the synthetic peptide has the amino acid sequence of SEQ ID NO: 19 (herein after 7-mer (D→N)). In other example, the synthetic peptide has the amino acid sequence of SEQ ID NO: 20 (herein after 7-mer (D→F)). IN a further example, the synthetic peptide has the amino acid sequence of SEQ ID NO: 21 (herein after 7-mer (D→L)).

The diseases, disorders or conditions related to inflammation treatable by the present medicament or composition is selected from the group consisting of, autoimmune disease, acne rosacea, peptic ulcers, gastritis, gout, gouty arthritis, arthritis, inflammatory bowel disease, Crohn's disease, ulcerative colitis, ulcers, chronic bronchitis, asthma, allergy, allergic conjunctivitis, acute lung injury, pulmonary inflammation, airway hyper-responsiveness, vasculitis, septic shock, atopic dermatitis and eczema.

According to some embodiments, the present medicament or composition is suitable for treating autoimmune disease, which is any of psoriasis, rheumatoid arthritis, systemic lupus erythematosus, ulcerative colitis, Crohn's disease, transplant rejection, immune disorder associated with graft transplantation rejection, benign lymphocytic angiitis, lupus erythematosus, Hashimoto's thyroiditis, primary myxedema, Graves's disease, pernicious anemia, autoimmune atrophic gastritis, Addison's disease, insulin dependent diabetes mellitis, Good pasture's syndrome, muasthenia gravis, pemphigus, sympathetic ophthalmia, autoimmune uveitis, autoimmune hemolytic anemia, idiopathic thrombocytopenia, primary biliary cirrhosis, chronic hepatitis, ulcerates colitis, Sjogren's syndrome, Wegener's sarcoidosis, antiphospholipid syndrome, inflammatory myopathy, polyarteritis, rheumatic disease, polymyositis, scleroderma, mixed connective tissue disease, inflammatory rheumatism, degenerative rheumatism, extra-articular rheumatism, collagen disease, chronic polyarthritis, psoriasis arthropathica, ankylosing spondylitis, juvenile rheumatoid arthritis, periarthritis humeroscapularis, panarteriitis nodosa, progressive systemic scleroderma, arthritis urica, dermatomyositis, muscular rheumatism, myositis, myogelosis, and chondrocalcinosis, thyroiditis, allergic oedema, granulomas, Alzheimer's disease, Parkinson's disease, multiple sclerosis, or amyotrophic lateral sclerosis (ALS).

In some examples, the autoimmune disease is psoriasis.

In other examples, the autoimmune disease is rheumatoid arthritis.

According to some embodiments, the disease, disorder or condition related to inflammation is asthma.

According to other embodiments, the disease, disorder or condition related to inflammation is allergic conjunctivitis.

The medicament or composition of the present disclosure may be administered to the subject via intravascular delivery (e.g., injection or infusion), oral, enteral, rectal, pulmonary (e.g., inhalation), nasal, topical (including transdermal, buccal and sublingual), intravesical, intravitreal, intraperitoneal, vaginal, brain delivery (e.g., intracerebroventricular, and intracerebral), CNS delivery (e.g., intrathecal, perispinal, and intra-spinal) or parenteral (e.g., subcutaneous, intramuscular, intravenous, and intradermal), transmucosal administration or administration via an implant, or other delivery routes known in the art.

The third aspect of the present disclosure is thus directed to a method of treating a subject suffering from a disease, a disorder and/or a condition related to inflammation. The method comprises the step of, administering to the subject a medicament or a composition of the present disclosure described above for ameliorating or alleviating symptoms related to the disease, disorder and/or condition related to inflammation.

According to preferred embodiments, the disease, disorder and/or condition related to inflammation treatable by the present method is selected from the group consisting of, autoimmune disease, acne rosacea, peptic ulcers, gastritis, gout, gouty arthritis, arthritis, inflammatory bowel disease, Crohn's disease, ulcerative colitis, ulcers, chronic bronchitis, asthma, allergy, allergic conjunctivitis (AC), acute lung injury, pulmonary inflammation, airway hyper-responsiveness, vasculitis, septic shock, atopic dermatitis and eczema.

According to preferred examples, the autoimmune disease that is treatable by the present method is selected from the group consisting of, psoriasis, rheumatoid arthritis, systemic lupus erythematosus, ulcerative colitis, Crohn's disease, transplant rejection, immune disorder associated with graft transplantation rejection, benign lymphocytic angiitis, lupus erythematosus, Hashimoto's thyroiditis, primary myxedema, Graves's disease, pernicious anemia, autoimmune atrophic gastritis, Addison's disease, insulin dependent diabetes mellitus, Good pasture's syndrome, muasthenia gravis, pemphigus, sympathetic ophthalmia, autoimmune uveitis, autoimmune hemolytic anemia, idiopathic thrombocytopenia, primary biliary cirrhosis, chronic hepatitis, ulcerates colitis, Sjogren's syndrome, Wegener's sarcoidosis, antiphospholipid syndrome, inflammatory myopathy, polyarteritis, rheumatic disease, polymyositis, scleroderma, mixed connective tissue disease, inflammatory rheumatism, degenerative rheumatism, extra-articular rheumatism, collagen disease, chronic polyarthritis, psoriasis arthropathica, ankylosing spondylitis, juvenile rheumatoid arthritis, periarthritis humeroscapularis, panarteriitis nodosa, progressive systemic scleroderma, arthritis urica, dermatomyositis, muscular rheumatism, myositis, myogelosis, and chondrocalcinosis, thyroiditis, allergic oedema, granulomas, Alzheimer's disease, Parkinson's disease, multiple sclerosis, or amyotrophic lateral sclerosis (ALS).

In some examples, the autoimmune disease is psoriasis.

In other examples, the autoimmune disease is rheumatoid arthritis.

According to some embodiments, the disease, disorder or condition related to inflammation is asthma.

According to other embodiments, the disease, disorder or condition related to inflammation is allergic conjunctivitis.

According to optional embodiments, the method further includes the step of, administered to the subject an effective amount of an anti-inflammatory agent. Preferably, the anti-inflammatory agent is a non-steroid anti-inflammatory drug (NSAID).

In all embodiments, the subject is a human.

The details of one or more embodiments of the invention are set forth in is the accompanying description below. Other features and advantages of the invention will be apparent from the detail descriptions, and from claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The present description will be better understood from the following detailed description read in light of the accompanying drawings, where.

DESCRIPTION OF THE INVENTION

Figure 1:
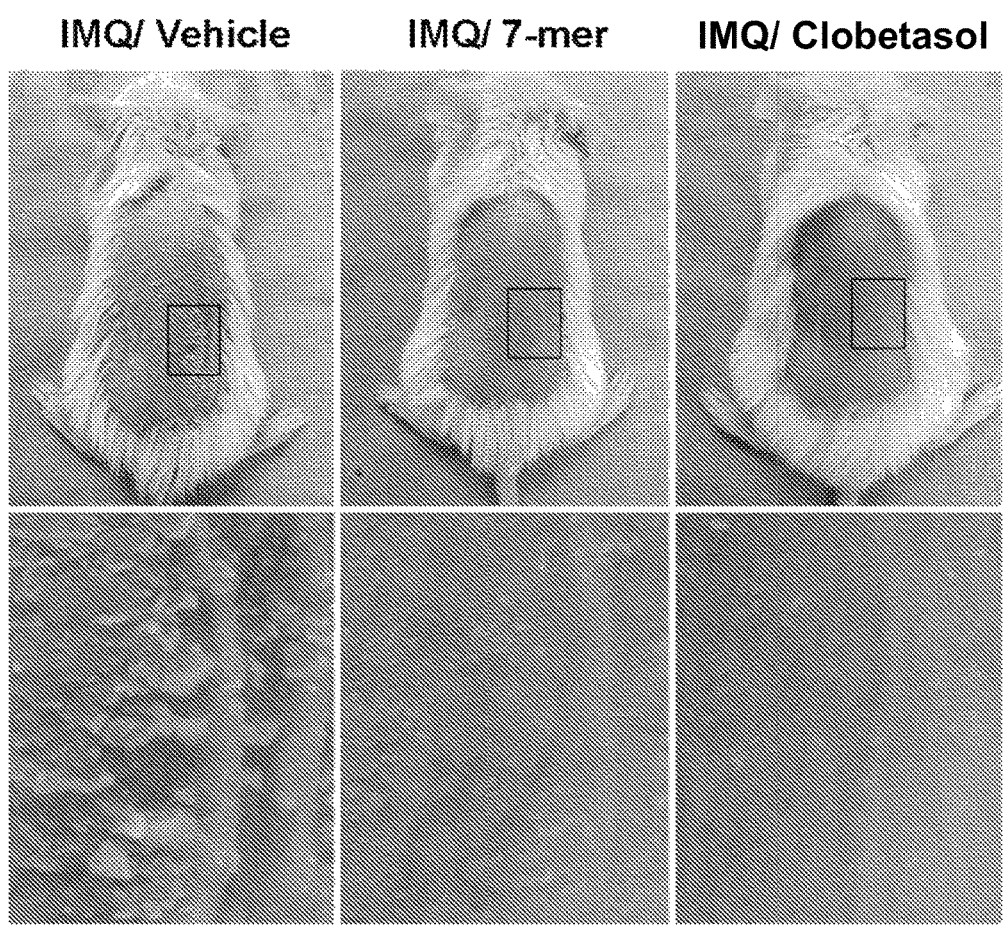
FIG. 1 are photographs depicting the effect of 7-mer on IMQ-induced psoriasis-like skin inflammation in accordance with one embodiment of the present disclosure, with each inserts being the photograph taken at high-powered light-field camera of the back skin.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

As used herein, the term "peptide" denotes a polymer of amino acid residues. By the term "synthetic peptide" as used herein, it is meant a peptide which does not comprise an entire naturally occurring protein molecule. The peptide is "synthetic" in that it may be produced by human intervention using such techniques as chemical synthesis, recombinant genetic techniques, or is fragmentation of whole antigen or the like. Throughout the present disclosure, the positions of any specified amino acid residues within a peptide are numbered starting from the N terminus of the peptide. When amino acids are not designated as either D- or L-amino acids, the amino acid is either L-amino acid or could be either D- or L-amino acid, unless the context requires a particular isomer. The terms "D-amino acid" and "L-amino acid" are used to refer to absolute configuration of the amino acid, rather than a particular direction of rotation of plane-polarized light. The usage herein is consistent with standard usage by those skilled in the related art. Amino acids are designated herein using standard 1-letter or 3-letter codes, e.g., as designated in Standard ST.25 in the Handbook On Industrial Property Information and Documentation.

As discussed herein, minor variations in the amino acid sequences of proteins/peptides are contemplated as being encompassed by the presently disclosed and claimed inventive concept(s), providing that the variations in the amino acid sequence maintain at least 90%, such as at least 70%, 71%, 72%, 73%, 75%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99%. The present synthetic peptide may be modified specifically to alter a feature of the peptide unrelated to its physiological activity. For example, certain amino acids can be changed and/or deleted without affecting the physiological activity of the peptide in this study (i.e., its ability to treat inflammation related diseases and/or conditions). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of proteins/peptides can be readily prepared by those of ordinary skill in the art. Preferred amino- and carboxy-termini of fragments or analogs occur near boundaries of functional domains. In one example, one amino acid residue (e.g., valine) of the present synthetic peptide is conservatively replaced (e.g., by leucine). In other examples, two amino acid residues of the present synthetic peptide are conservatively replaced by other suitable amino acid residues, for example, valine (V) and arginine (R) are replaced by the pair of amino acids that includes, but is not limited to, methionine (M) and lysine (K), lysine (K) and proline (P), tryptophan (W) and isoleucine (I), isoleucine (I) and proline (P), asparagine (N) and valine (V), and glutamine (G) and lysine (K).

The term "treatment" as used herein are intended to mean obtaining a desired pharmacological and/or physiologic effect. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition from occurring in an individual who may be pre-disposed to the disease but has not yet is been diagnosed as having it; (2) inhibiting a disease (e.g., by arresting its development); or (3) relieving a disease (e.g., reducing symptoms associated with the disease).

The term "administered", "administering" or "administration" are used interchangeably herein to refer a mode of delivery, including, without limitation, intraveneously, intramuscularly, intraperitoneally, intraarterially, intracranially, intraconjunctiva, or subcutaneously administering an agent (e.g., a compound or a composition) of the present invention.

The term "an effective amount" as used herein refers to an amount effective, at dosages, and for periods of time necessary, to achieve the desired result with respect to the treatment of a disease. For example, in the treatment of an allergic disease, an agent (i.e., a compound, a synthetic peptide, or a nucleic acid encoding a therapeutic peptide) which decrease, prevents, delays or suppresses or arrests any symptoms of the inflammation or allergic disease would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

The term "subject" or "patient" is used interchangeably herein and is intended to mean a mammal including the human species that is treatable by the synthetic peptide and/or method of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the is present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human.

The term "pharmaceutically acceptable carrier, excipient or stabilizer" as used herein is meant a suitable vehicle, agent or compound which is pharmaceutically acceptable for skin or ophthalmic administration.

As used herein, the term "diseases, disorders and/or conditions related to inflammation" means pathological diseases, disorders and/or conditions that involve immune responses for the disease progression or symptom manifestation.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Detail Description of Preferred Embodiments

The present disclosure is based, at least in part, on the discovery of short synthetic peptides that are capable of treating and/or preventing a subject from developing a disease or a condition related to inflammation. Accordingly, this invention provides method and composition comprising the newly identified synthetic peptides for the treatment and/or prophylaxis of a disease or a condition related to inflammation.

2.1 The Present Synthetic Peptides

The short synthetic peptide of the present disclosure consists of 7 consecutive amino acid residues set forth as $X_1X_2X_3X_4X_5X_6X_7$ (SEQ ID NO: 1), wherein, $X_1$ is alanine (A), aspartic acid (D), asparagine (N), leucine (L), phenylalanine (F), or valine (V);
$X_2$ is alanine (A), isoleucine (I), leucine (L), or valine (V);
$X_3$ is phenylalanine (F), tyrosine (Y) or tryptophan (W);
$X_4$ is arginine (R) or lysine (K);
$X_5$ is valine (V), methionine (M), isoleucine (I), leucine (L), or glutamine (Q);
$X_6$ is arginine (R), glutamine (Q), lysine (K) or proline (P);
$X_7$ is serine (S) or threonine (T); and
each $X_2$, $X_3$, $X_4$, $X_6$ and $X_7$ are independently L-form amino acid residues.

According to some embodiments, at least one of $X_1$ and $X_5$ is a D-form amino acid residue, and the synthetic peptide has the amino acid sequence of SEQ ID NO: 2. In one example, $X_1$ is in D-form, such as D-aspartic acid (hereinafter 7-mer DD). In another example, $X_5$ is in D-form, such as D-valine (hereinafter 7-mer DV).

According to other preferred embodiments, the synthetic peptide has the amino acid sequence that is SEQ ID NOs: 3 or 4. In one example, the synthetic peptide has the amino acid sequence of SEQ ID NO: 3 (herein after 7-mer Da). In another example, the synthetic peptide has the amino acid sequence of SEQ ID NO: 4 (herein after 7-mer La).

According to other preferred embodiments, the synthetic peptide has the amino acid sequence that is any of SEQ ID NOs: 10, 11, 12, 13, 14, 15, 16, 17, 18, 19, 20 or 21. In one example, the synthetic peptide has the amino acid sequence of SEQ ID NO: 10 (herein after 7-mer MK). In another example, the synthetic peptide has the amino acid sequence of SEQ ID NO: 11 (herein after 7-mer KP). In yet another example, the synthetic peptide has the amino acid sequence of SEQ ID NO: 12 (herein after 7-mer WI). In a further example, the synthetic peptide has the amino acid sequence of SEQ ID NO: 13 (herein after 7-mer IP). In still a further example, the synthetic peptide has the amino acid sequence of SEQ ID NO: 14 (herein after 7-mer NV). In yet a further example, the synthetic peptide has the amino acid sequence of SEQ ID NO: 15 (herein after 7-mer QK). In another example, the synthetic peptide has the amino acid sequence of SEQ ID NO: 16 (herein after 7-mer VFT). In yet a further example, the synthetic peptide has the amino acid sequence of SEQ ID NO: 17 (herein after 7-mer (V→L)). In still a further example, the synthetic peptide has the amino acid sequence of SEQ ID NO: 18 (herein after 7-mer (R2→Q)). In another example, the synthetic peptide has the amino acid sequence of SEQ ID NO: 19 (herein after 7-mer (D→N)). In other example, the synthetic peptide has the amino acid sequence of SEQ ID NO: 20 (herein after 7-mer (D→F)). In a further example, the synthetic peptide has the amino acid sequence of SEQ ID NO: 21 (herein after 7-mer (D→L)).

According to some embodiments, serine (S) residues located at the C-terminus of SEQ ID NO: 2 is deleted, and the resulted peptide designated as the control peptide (DLYRVR, SEQ ID NO: 22) does not possess any biological function in the present study. Accordingly, serine (S) residue located at the C-terminus of SEQ ID NO: 2 is necessary for the biological activity of the present synthetic peptide for the treatment and/or prophylaxis of a disease and/or a condition related to inflammation, this residues can only be substituted by conservative amino acid residues, but may not be deleted.

According to some embodiments of the present disclosure, at least one D-form amino acid residues is included in SEQ ID NO: 2, which gives rise to D-form analogues of the 7-mer (i.e., 7-mer DD, and 7-mer DV) as described in the Table 1 of Example 1 of this application. Among these D-form analogues, it is found that tyrosine (Y), arginine (R) and serine (S) of the 7-mer (SEQ ID NO: 2) must remain in L-form, or else the resulted peptide (i.e., 7-mer DL, 7-mer DY, 7-mer DR, 7-mer DR2, and 7-mer DS, see Table 1 of Example 1) will lose its biological activity towards autoimmune diseases and/or inflammatory disorders.

According to other embodiments of the present disclosure, each amino acid residues of the 7-mer are independently replaced by alanine (A), which give rise to 7-mer analogues (i.e., 7-mer Da, and 7-mer La) as described in the Table 1 of Example 1 of this application. Among these analogues, it is found that aspartic acid (D) and leucine (L) of the 7-mer (SEQ ID NO: 2) may be replaced by alanine (A) without losing its biological activity towards diseases and/or conditions related to inflammation, and/or fibrosis, whereas replacing any of the rest of amino acid residues of the 7-mer (i.e., amino acid residues at positions 3 to 7 of the 7-mer) results in the loss of the bioactivity of the 7-mer.

According to further embodiments of the present disclosure, at least two of the amino acid residues of the 7-mer are independently replaced by other amino acid residues, which give rise to 7-mer analogues (i.e., 7-mer MK, 7-mer KP, 7-mer WI, 7-mer IP, 7-mer NV, 7-mer QK, 7-mer VFT, 7-mer (V→L), 7-mer (R2→Q), 7-mer (D→V), 7-mer (D→F) and 7-mer (D→L)) as described in the Table 1 of Example 1 of this application. It is found that each of the 7-mer analogues created by site specific replacement still possesses some level of bioactivity of the 7-mer peptide, among which, each of 7-mer VFT, 7-mer (V→L), 7-mer (D→V), 7-mer (D→F) and 7-mer (D→L) exhibits relatively the same bioactivity that is similar to the 7-mer (SEQ ID NO: 2).

The present synthetic peptide may be synthesized in accordance with is any standard peptide synthesis protocol in the art. In one embodiment, the present synthetic peptides were synthesized by use of a solid-phase peptide synthesizer (ABI433A peptide synthesizer, Applied Biosystems Inc., Life Technologies Corp., Foster City, Calif., USA) in accordance with the manufacturer's protocols.

Alternatively, the present synthetic peptides may be prepared using recombinant technology. For example, one can clone a nucleic acid encoding the present peptide in an expression vector, in which the nucleic acid is operably linked to a regulatory sequence suitable for expressing the present peptide in a host cell. One can then introduce the vector into a suitable host cell to express the peptide. The expressed recombinant polypeptide can be purified from the host cell by methods such as ammonium sulfate precipitation and fractionation column chromatography. A peptide thus prepared can be tested for its activity according to the method described in the examples below.

The above-mentioned nucleic acids or polynucleotide can be delivered by the use of polymeric, biodegradable microparticle or microcapsule delivery devices known in the art. Another way to achieve uptake of the nucleic acid in a host is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

The present synthetic peptide may be modified at its N-terminus or C-terminus. Examples of N-terminal modifications include, but are not limited to, N-glycated, N-alkylated, and N-acetylated amino acid. A terminal modification is can include a pegylation. An example of C-terminal modification is a C-terminal amidated amino acid. Alternatively, one or more peptide bond may be replaced by a non-peptidyl linkage, the individual amino acid moieties may be modified through treatment with agents capable of reacting with selected side chains or terminal residues.

Various functional groups may also be added at various points of the synthetic peptide that are susceptible to chemical modification. Functional groups may be added to the termini of the peptide. In some embodiments, the function groups improve the activity of the peptide with regard to one or more characteristics, such as improving the stability, efficacy, or selectivity of the synthetic peptide; improving the penetration of the synthetic peptide across cellular membranes and/or tissue barrier; improving tissue localization; reducing toxicity or clearance; and improving resistance to expulsion by cellular pump and the like. Non-limited examples of suitable functional groups are those that facilitate transport of a peptide attached thereto into a cell, for example, by reducing the hydrophilicity and increasing the lipophilicity of the peptide, these functional groups may optionally and preferably be cleaved in vivo, either by hydrolysis or enzymatically, inside the cell. Hydroxy protecting groups include esters, carbonates and carbamate protecting groups. Amine protecting groups include alkoxy and aryloxy carbonyl groups. Carboxylic acid protecting groups include aliphatic, benzylic and aryl esters. In some optional embodiments, the carboxylic acid group in the side chain of the aspartic acid (D) of the present synthetic peptide is protected, preferably, by a methyl, ethyl, benzyl, or substituted benzyl ester.

A "peptidomimetic organic moiety" can optionally be substituted for amino acid residues in the present synthetic peptide both as conservative and as non-conservative substitutions. The peptidomimetic organic moieties optionally and preferably have steric, electronic or configuration properties similar to the replaced amino acid and such peptidomimetics are used to replace amino acids in is the essential positions, and are considered conservative substitutions.

Peptidomimetics may optionally be used to inhibit degradation of peptides by enzymatic or other degradative processes. The peptidomimetics can optionally and preferably be produced by organic synthetic techniques. Non-limiting examples of suitable petidomimetics include isosteres of amide bonds, 3-amino-2-propenidone-6-carboxylic acid, hydroxyl-1,2,3,4-tetrahydro-isoquinoline-3-carboxylate, 1,2,3,4-tetrahydro-isoquinoline-3-carboxylate, and histidine isoquinolone carboxylic acid.

Any part of the synthetic peptide may optionally be chemically modified, such as by the addition of functional groups. The modification may optionally be performed during the synthesis of the present peptide. Non-limiting exemplary types of the modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxy groups to an amino group of a sugar. Acetal and ketal bonds can also optionally be formed between amino acids and carbon hydrates.

2.2 Compositions for the Treatment and/or Prophylaxis of Diseases and/or Conditions Related to Inflammation The present synthetic peptides are suitable for treating a subject suffering from a disease and/or a condition related to inflammation, or preventing a subject from developing the disease and/or condition related to inflammation.

Accordingly, a further aspect of the present disclosure is to provide a medicament comprising the present synthetic peptide for treating a disease, a disorder and/or a condition related to inflammation, which include and are not limited to, autoimmune disease, acne rosacea, peptic ulcers, gastritis, gout, gouty arthritis, arthritis, inflammatory bowel disease, Crohn's disease, ulcerative colitis, ulcers, chronic bronchitis, asthma, allergy, allergic conjunctivitis, acute lung injury, pulmonary inflammation, airway hyper-responsiveness, vasculitis, septic shock, atopic dermatitis and eczema.

In some embodiments, the medicament comprising the present synthetic peptide is for treating the autoimmune disease. Non-limiting examples of autoimmune disease which may be treated by the medicament comprising the present synthetic peptide are psoriasis, rheumatoid arthritis, systemic lupus erythematosus, ulcerative colitis, Crohn's disease, transplant rejection, immune disorder associated with graft transplantation rejection, benign lymphocytic angiitis, lupus erythematosus, Hashimoto's thyroiditis, primary myxedema, Graves's disease, pernicious anemia, autoimmune atrophic gastritis, Addison's disease, insulin dependent diabetes mellitus, Good pasture's syndrome, muasthenia gravis, pemphigus, sympathetic ophthalmia, autoimmune uveitis, autoimmune hemolytic anemia, idiopathic thrombocytopenia, primary biliary cirrhosis, chronic hepatitis, ulcerates colitis, Sjogren's syndrome, Wegener's sarcoidosis, antiphospholipid syndrome, inflammatory myopathy, polyarteritis, rheumatic disease, polymyositis, scleroderma, mixed connective tissue disease, inflammatory rheumatism, degenerative rheumatism, extra-articular rheumatism, collagen disease, chronic polyarthritis, psoriasis arthropathica, ankylosing spondylitis, juvenile rheumatoid arthritis, periarthritis humeroscapularis, panarteriitis nodosa, progressive systemic scleroderma, arthritis urica, dermatomyositis, muscular rheumatism, myositis, myogelosis, and chondrocalcinosis, thyroiditis, allergic oedema, granulomas, Alzheimer's disease, Parkinson's disease, multiple sclerosis, or amyotrophic lateral sclerosis (ALS).

In one example, the autoimmune disease is psoriasis. In another example, the autoimmune disease is rheumatoid arthritis.

In another embodiment, the medicament comprising the present synthetic peptide is for the treatment of a disease, a disorder and/or a condition related to inflammation is an allergic disease. Non-limiting examples of the allergic disease which may be treated by the medicament comprising the present is synthetic peptide are asthma, allergy, and allergic conjunctivitis.

In one example, the allergic disease is asthma. In another example, the allergic disease is allergic conjunctivitis.

The medicament is manufactured by mixing suitable amount of the present synthetic peptide with a pharmaceutically acceptable carrier, excipient or stabilizer into a composition. In particular embodiments, the synthetic peptide is selected from the group of peptides as described above, which include but are not limited to, 7-mer, 7-mer DD, 7-mer DV, 7-mer Da, 7-mer La, 7-mer MK, 7-mer KP, 7-mer WI, 7-mer IP, 7-mer NV, 7-mer 7-mer QK, 7-mer LQ, 7-mer VFT, and a combination thereof.

The amount of the peptide present in the medicament or the composition will depend on the peptide used. The peptide typically will be present in the composition in the amount from about 0.001% to about 10% by weight, such as 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2., 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0% by weight; in particular in an amount from about 0.01% to about 5% by weight, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2., 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0% by weight.

Pharmaceutical acceptable carriers, excipients or stabilizers for use with the synthetic peptides are well known in the relevant art, and include but are not limited to non-toxic inert solid, semi-solid, or liquid filler, diluent, encapsulating agent or formulation auxiliary. Typical pharmaceutically acceptable carrier is is water or physiological saline. Examples of pharmaceutically acceptable carriers include, but are not limited to, sugars such as lactose, glucose, and sucrose; starches such as corn starch; cellulose and its derivatives such as carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; as well as other agents such as non-toxic lubricants (e.g., lauryl sulfate and magnesium stearate), coloring agents, releasing agents, flavoring agents, preservatives and antioxidants.

Suitable routes of administration of the medicament or the composition of the present invention are intravascular delivery (e.g., injection or infusion), oral, enteral, rectal, pulmonary (e.g., inhalation), nasal, topical (including transdermal, buccal and sublingual), intravesical, intravitreal, intraperitoneal, vaginal, brain delivery (e.g., intracerebroventricular, and intracerebral), CNS delivery (e.g., intrathccal, perispinal, and intra-spinal) or parenteral (e.g., subcutaneous, intramuscular, intravenous, and intradermal), transmucosal administration or administration via an implant, or other delivery routes known in the art.

Pharmaceutical composition suitable for oral administration may be formulated into discrete dosage units such as pills, tablets, lozenges or hard or soft capsules, or as a dispersible powder or granules, or as a solutions or suspension for example, aqueous or oily suspensions, emulsions, syrups, elixirs, or enteral formulas. The composition may be presented in uni-dose or multi-dose containers, such as sealed vials or ampoules, and may be stored in a lyophilized condition requiring the addition of sterile liquid carrier (e.g., water or saline) prior to use.

Pharmaceutical composition suitable for parental administration may be formulated into aqueous or non-aqueous sterile injection by mixing or dispersing is the present synthetic peptide with a sterile solvent, such as water, Ringer's solution, saline, 1,3-butanediol, alcohol and etc. Alternatively, fixed oil, fatty acid or synthetic mono- or diglycerides may be used as the solvent. The composition may be sterilized by filtering through a filter.

For topical or transdermal application, the pharmaceutical composition is generally formulated into ointments, pastes, creams, lotions, gels, patches or sprays. Ophthalmic formulations, ear drops, and eye drops are also contemplated within the scope of the invention. According to some embodiments, compositions of the invention are administered topically to the eye. Depending on the type and severity of the disease, about 1 µg/kg to about 50 mg/kg (e.g., 0.1-20 mg/kg) of the present synthetic peptide is administered to the patient. A typical daily or weekly dosage might range from about 1 µg/kg to about 20 mg/kg or more. The doses utilized for any of the above-described purposes of topical administration will generally be from about 0.01 to about 100 mg per kilogram of body weight (mg/kg), administered one to several, e.g., four, six, eight or even more, times per day.

Pharmaceutical composition suitable for pulmonary administration is formulated as find dusts or mists which may be generated by means of metered dose pressurized aerosols, nebulisers or insufflators.

The pharmaceutical composition provided by the invention preferably is presented in the form of a kit. In the present invention, a "kit" is understood as a product containing the synthetic peptide(s) provided by the present invention and/or the additional therapeutic compounds forming the packaged composition such that the transport, storage and simultaneous or successive administration thereof is allowed. Therefore, the kits of the invention can contain one or more sealed ampoules respectively contain the synthetic peptides of the invention, and which can be prepared in a single dose or as multiple doses. The kit can additionally contain a vehicle suitable for solubilizing the synthetic peptides such is as aqueous media such as saline solution, Ringer's solution, dextrose and sodium chloride; water-soluble media such as alcohol, polyethylene glycol, propylethylene glycol; and water-insoluble vehicles if necessary. Another component which may be present in the kit is a package which allows maintaining the compositions of the invention within determined limits. Materials suitable for preparing such packages include glass, plastic (polyethylene, polypropylene, polycarbonate and the like), bottles, vials, paper, sachets and the like.

The kit of the invention can additionally contain instructions for the simultaneous, successive or separate administration of the different formulations present in the kit. Therefore, the kit of the invention can further comprise instructions for the simultaneous, successive or separate administration of the different components. Said instructions can be in the form of printed material or in the form of an electronic support which can store the instructions such that they can be read by a subject, such as electronic storage media (magnetic disks, tapes and the like), optical media (CD-ROM, DVD) and the like. The media can additionally or alternatively contain Internet webpages providing said instructions.

2.3 Methods for the Treatment and/or Prophylaxis of Diseases, Disorders and/or Conditions Related to Inflammation As it has been indicated above, the findings described in the present invention are useful for the prevention and/or treatment of diseases, disorders and/or conditions related to inflammation.

The present invention therefore relates to a method for the prevention and/or treatment of diseases, disorders and/or conditions related to inflammation, which comprises administering to a subject in need thereof a medicament or a composition described above, which comprises a synthetic peptide consisting of 7 consecutive amino acid residues set forth as $X_1X_2X_3X_4X_5X_6X_7$ (SEQ ID NO: 1), wherein, $X_1$ is alanine (A), aspartic acid (D), asparagine (N), leucine (L), is phenylalanine (F), or valine (V);

$X_2$ is alanine (A), isoleucine (I), leucine (L), or valine (V);

$X_3$ is phenylalanine (F), tyrosine (Y) or tryptophan (W);

$X_4$ is arginine (R) or lysine (K);

$X_5$ is valine (V), methionine (M), isoleucine (I), leucine (L), or glutamine (Q);

$X_6$ is arginine (R), glutamine (Q), lysine (K) or proline (P);

$X_7$ is serine (S) or threonine (T); and each $X_2$, $X_3$, $X_4$, $X_6$ and $X_7$ are independently L-form amino acid residues; and a pharmaceutically acceptable carrier. The medicament and/or composition when administrated to the subject is capable of ameliorating or alleviating the symptoms associated to the diseases, disorders and/or conditions related to inflammation.

In particular embodiments, the synthetic peptide is selected from the group of peptides described above, which include and are not limited to, 7-mer, 7-mer DD, 7-mer DV, 7-mer Da, 7-mer La, 7-mer MK, 7-mer KP, 7-mer WI, 7-mer IP, 7-mer NV, 7-mer QK, 7-mer VFT, 7-mer (V→L), 7-mer (R2→Q), 7-mer (D→V), 7-mer (D→F), 7-mer (D→L), and a combination thereof.

The diseases, disorders and/or conditions related to inflammation include, and are not limited to, autoimmune disease, acne rosacea, peptic ulcers, gastritis, gout, gouty arthritis, arthritis, inflammatory bowel disease, Crohn's disease, ulcerative colitis, ulcers, chronic bronchitis, asthma, allergy, allergic conjunctivitis, acute lung injury, pulmonary inflammation, airway hyper-responsiveness, vasculitis, septic shock, atopic dermatitis and eczema.

In some embodiments, the disease, disorder and/or condition related to inflammation treatable by the present method is autoimmune disease. Non-limiting examples of autoimmune disease which may be treated by the preset method are psoriasis, rheumatoid arthritis, systemic lupus erythematosus, ulcerative colitis, Crohn's disease, transplant rejection, immune disorder associated with graft transplantation rejection, benign lymphocytic angiitis, lupus is erythematosus, Hashimoto's thyroiditis, primary myxedema, Graves's disease, pernicious anemia, autoimmune atrophic gastritis, Addison's disease, insulin dependent diabetes mellitis, Good pasture's syndrome, muasthenia gravis, pemphigus, sympathetic ophthalmia, autoimmune uveitis, autoimmune hemolytic anemia, idiopathic thrombocytopenia, primary biliary cirrhosis, chronic hepatitis, ulcerates colitis, Sjogren's syndrome, Wegener's sarcoidosis, antiphospholipid syndrome, inflammatory myopathy, polyarteritis, rheumatic disease, polymyositis, scleroderma, mixed connective tissue disease, inflammatory rheumatism, degenerative rheumatism, extra-articular rheumatism, collagen disease, chronic polyarthritis, psoriasis arthropathica, ankylosing spondylitis, juvenile rheumatoid arthritis, periarthritis humeroscapularis, panarteriitis nodosa, progressive systemic scleroderma, arthritis urica, dermatomyositis, muscular rheumatism, myositis, myogelosis, and chondrocalcinosis, thyroiditis, allergic oedema, granulomas, Alzheimer's disease, Parkinson's disease, multiple sclerosis, or amyotrophic lateral sclerosis (ALS).

In one example, the autoimmune disease is psoriasis. In another example, the autoimmune disease is rheumatoid arthritis.

In other embodiments, the disease, disorder and/or condition related to inflammation treatable by the present method is an allergic disease. Non-limiting examples of the allergic disease which may be treated by the present method are asthma, allergy, and allergic conjunctivitis.

In one example, the allergic disease is asthma. In another example, the allergic disease is allergic conjunctivitis.

Optionally, the present method may further include administering to the subject an effective amount of an anti-inflammatory agent, for treating diseases, disorders and/or conditions related to inflammation.

According to embodiments of the present disclosure, the anti-inflammatory agent may be a steroid (e.g., corticosteroid), a non-steroidal anti-inflammatory drug (NSAID), an immunosuppressant, or a tumor necrosis is factor (TNF).

Non-limiting examples of corticosteroid include, but are not limited to, prednisone, dexamethasone, hydrocortisone, and methylprednisolone.

The NSAID may be selected from the group consisting of, naproxen, ibuprofen, ketorolac, ketoprofen, fenoprofen, flurbiprofen, oxaprofen, diclofenac, tolmetin, tolfenamic add, mefenamic acid, sulindac, indomethacin, salicylic acid, acetylsalicylic acid, diflunisal, loxoprofen, indoprofen, pirprofen, clidanac, fenciorac, meclofenamate, benoxaprofen, carprofen, isofezolac, aceclofenac, fenbufen, etodolac acid, fleclozic acid, amfenac, mefenamic adic, bromfenac, flenclofenac, alcofenac, orpanoxin, zomepirac, flufenamic acid, niflumic add, pranoprofen, zaltoprofen, and suprofen. Preferred NSAID is diclofenac, naproxen or ibuprofen, for either drugs is the most potent and prescribed NSAID.

The immunosuppressant may be glucocorticoids, cytostatics (e.g., alkylating agents or antimetabolites), antibodies, drugs that act on immunophilins (e.g., cyclosporin, Tacrolimus, Sirolimus), interferons, TNF-binding proteins, mycophenolate mofetil, and etc. Non-limiting examples of alkylating agents include, but are not limited to, cyclophosphamides, nitrosoureas, and platinum compounds. Non-limiting examples of antimetabolites include, but are not limited to, methotrexate, azathiopurine, mercaptopurine, and fluorouracil.

In all embodiments, the subject suitable for treatment is a human.

The present invention will now be described more specifically with reference to the following embodiments, which are provided for the purpose of demonstration rather than limitation.

EXAMPLES

Materials and Methods

Materials

Dulbecco's modified Eagle's medium (DMEM), fetal bovine serum (FBS), 0.25% trypsin, antibiotic-antimicotic solutions were purchased from Invitrogen (Carlsbad, Calif.). 3-(4,5-cimethylthiazol-2-yl)-2,5-diphenyl tetrazolium bromide (MTT) was from Merck (Catalog number 1.11714.0001). Dimethyl sulfoxide (DMSO), hypochlorous acid, 5-bromo-2'-deoxyuridine (BrdU), Hoechst 33258 dye, NaClO solution and Periodic acid-Schiff (PAS) reagent were all from Sigma-Aldrich (St. Louis, Mo.). Anti-BrdU was from GeneTex (Taipei, Taiwan). IMQ cream (ALDARA CREAM 5%) was purchased from DKSH (Taipei, Taiwan).

All peptides were synthesized by GenScript (Piscataway, N.J., USA), in which each peptide was modified by acetylation at the $NH_2$ termini and amidation at the COOH termini to improve its stability, and was subsequently characterized using mass spectrometry (>95% purity).

Cell Culture and Treatment

The murine macrophage cell line RAW264.7 (ATCC, Rockville, Md.) was maintained in DMEM supplemented with 10% FBS and antibiotic-antimicotic solutions. Cells were cultured at 37° C. and 5% $CO_2$.

Experimental Animals

All animals were maintained in the animal facility in accordance with the procedures approved by Mackay Memorial Hospital Review Board (Taiwan, R.O. C.). All animal experimental procedures were conducted according to the ARVO Statement for the Use of Animals in Ophthalmic and Vision Research.

MTT Assay

RAW264.7 cells were seeded in 48-well culture plates ($2 \times 10^4$ cells/well) for 24 hrs and then cultured in serum-free DMEM for another 24 hrs before stimulation. For treatment, cells were exposed to 0.5 mL fresh serum-free DMEM medium containing 25 µM peptide for 24 hrs. To determine the cell viability, 50 µl of the MTT stock solution (5 mg MTT dissolved in 1 ml of sterile PBS) was added to each well. In addition, 50 µL of the MTT stock solution added to 500 µl of medium alone was included as a negative control. The plates were incubated at 37° C. for 4 hours. Aliquots (450 µl) from each sample were taken to a new well of 48-well culture plate, adding 100 µL DMSO, mixing thoroughly using the pipette is and reacted at 37° C. for 20 min and read absorbance at 570 nm.

Mouse Model of Psoriasis-Like Skin Inflammation

All experimental procedures were approved by the Mackay Memorial Hospital Animal Care and Uses Committee and conducted according to national animal welfare regulations. Psoriasis-like skin inflammation was created by treating mouse skin with Imiquimod (IMQ) in accordance with the procedures described by van der Fits et al (J Immunol. (2009), 182, 5836-5845). Accordingly, each BALB/c mice (8 weeks old) received a daily topical dose of 62.5 mg of commercially available IMQ cream (5%) on the shaved back and the right ear for 6 consecutive days; whereas the control mice (normal group) were treated with a control cream. For treatment, 7-mer analogue was mixed with IMQ cream to a concentration 100 µM.

Keratinocyte proliferation was determined by 5-bromo-2'-deoxyuridine (BrdU) incorporation. BrdU (Sigma-Aldrich) was reconstituted in DMSO as a stock solution of 80 mM. 10 µl of BrdU mixed with 90 µl of PBS was intraperitoneally injected into each mouse for 24 hr prior to euthanasia. Back skin was fixed overnight in 4% paraformaldehyde and embedded in paraffin for immunohistochemistry.

Rat Model of Rheumatoid Arthritis

In this study, acute arthritis was induced by direct injection of lipopolysaccharide (LPS) into rat joints in accordance with the procedures described by Pan R Y et al (J Virol. (1999) 73, 3410-3417). Briefly, adult (about 10 weeks old) male Sprague-Dawley rats (initial body wt=312±11 g) were anesthetized by an intraperitoneal injection of a Xylazine (10 mg/kg) and then randomly assigned to experimental groups; their right knees were later treated with a single intraarticular injection of 25 µl of 5% hyaluronic acid (HA) containing LPS (2 µg and 10 µg) or LPS+7-mer. 7-mer (10 mM stock) was dissolved in 25 µl of 5% HA to final concentration 1 mM. On day 2, the group LPS+7-mer or LPS+7-mer analogue was further treated with 7-mer by a single intraarticular is injection. On day 3, the knee joints were dissected and fixed in a 4% paraformaldehyde (PFA) solution and then decalcified with Shandon TBD-2 decalcifier (Thermo Scientific, Logan, Utah). The joints were then sectioned mid-sagittally and embedded in paraffin blocks. Sections (5 µm in thickness) were longitudinally cut, and stained with hematoxylin and eosin (H&E).

Mouse Model of Allergic Conjunctivitis

BALB/c mice (4- to 5-weeks old females) were sensitized intraperitoneally with 1 µg of ovalbumin (OVA) and 200 µl of 1.5% aluminum hydroxide (ALUM) on days 0 and 7, respectively; and then challenged two times topically in the conjunctival sac with 250 µg of OVA respectively on days 15 and 18. Control mice were given OVA with ALUM in sensitization stages, and PBS in place of OVA in challenge stages. For treatment, 7-mer was mixed with 1% CMC eye drop to a concentration 100 µM. After the OVA challenge (day 15), the mice were randomly assigned to two experimental groups (n=6 per group) and the eye was treated with 20 µl of 7-mer or vehicle eye drop twice a day for 4 days (to day 18). Twenty-four hrs after the final challenge with OVA (day 19), mice were euthanized and their eyes were harvested, fixed overnight in 4% paraformaldehyde and embedded in paraffin. To evaluate the eosinophilic infiltration, sections (5 µm) including eyelids were de-paraffinized and stained with acid-giemsa for detection of eosinophils.

Mouse Model of Allergic Asthma

BALB/c mice (4- to 5-weeks old females) were sensitized intraperitoneally with 1 µg of ovalbumin (OVA) and 200 µl of 1.5% aluminum hydroxide on days 0 and 7, respectively; and then challenged three times by intranasal injection with 250 µg of OVA on days 21, 22 and 23. Control mice were given OVA with ALUM in sensitization stages, and PBS in place of OVA in challenge stages. For treatment, 7-mer analogue was mixed with 1% CMC eye drop to a concentration 100 µM. On day 20 and after the OVA challenge (day 21), the mice were randomly assigned to two experimental groups (n=6 per group) is and the nasal was injected with 20 µl of 7-mer or vehicle drop twice a day for 4 days (to day 23). Twenty-four hrs after the final challenge with OVA (day 24), mice were euthanized and their eyes were harvested, fixed overnight in 4% paraformaldehyde and embedded in paraffin.

Mouse Model of Systemic Sclerosis (SSc)

Induction of SSc have been successfully established by subcutaneously injection with prooxidative agents (e.g., hypochlorous acid, HOCl) in BALB/c mice every day for 6 weeks (Servettaz A et al., J Immuno. 2009; 182: 5855).

To produce HOCl, 166 µl of NaClO solution (2.6% as active chlorine) was added to 11.1 ml of $KH_2PO_4$ solution (100 mM; pH 7.2). The concentration of HOCl was determined by spectrophotometry at 292 nm (molar absorption coefficient 350 $M^{-1}$ $cm^{-1}$). Female BALB/c mice (6 weeks old) were randomly distributed into experimental and control groups (n=6 per group). A total of 100 µl of HOCl solution mixed with 7-mer vehicle or 7-mer (final concentration 0.2 mM) was injected subcutaneously into the shaved back of the mice, using a 27-gauge needle, every day for 6 wks. Subcutaneous injection of phosphate-buffered saline (PBS) was served as normal control. Mice were euthanized and their skins were harvested, fixed overnight in 4% paraformaldehyde and embedded in paraffin. De-paraffinized skin sections were stained using Masson's Trichrome (Sigma-Aldrich, St. Louis, Mo.) procedure as described by the manufacturer.

Measurement of Total Collagens

Approximately 20% skin homogenate was used to determine the levels of soluble collagen. The collagen levels were quantified using a Sircol™ soluble collagen assay (Biocolor Ltd., Newtownabbey) according to the manufacturer's protocols. Briefly, 100 µl collected supernatant was mixed with 1 ml of Sircol dye for 30 minutes and centrifuged at the speed of 10,000 rpm for 10 minutes at room temperature to precipitate collagen-dye complex. The upper solution was decanted, and the pellets were dissolved in 1 mL Sircol alkali reagent and vortexed. Relative absorbance was measured at 540 nm.

Statistics

Results were expressed as the mean±standard error of the mean (SEM). 1-way ANOVA was used for statistical comparisons. $P<0.05$ was considered significant.

Example 1 Identification of the Functional Residues of the Present Synthetic Peptide In this example, a 7-mer peptide (SEQ ID NO: 2) was synthesized in accordance with the procedures described in the "Materials and Methods" section. Analogues of the 7-mer were created by "alanine scanning," "D-amino acid substitution" or site specific replacement, in which each indicated residues was replaced by alanine, its D-form counterpart or by replacing with specific amino acid residues.

Total of 25 peptides were synthesized, specifically, 7 analogues were created by "alanine scanning," they were termed 7-mer Da, 7-mer La, 7-mer Ya, 7-mer Ra, 7-mer Va, 7-mer R2a, and 7-mer Sa; and 7 analogues were created by "D-amino acid substitution," they were termed 7-mer DD, 7-mer DL, 7-mer DY, 7-mer DR, 7-mer DV, 7-mer DR2, and 7-mer DS; and additional 12 analogues were created by site specific replacement, they were termed 7-mer MK, 7-mer KP, 7-mer WI, 7-mer IP, 7-mer NV, 7-mer QK, 7-mer VFT, 7-mer (V→L), 7-mer (R2→Q), 7-mer (D→V), 7-mer (D→F), and 7-mer (D→L). Furthermore, a 6-mer control peptide was also synthesized, in which the serine (S) residue of the 7-mer was deleted. The respective sequences of the synthesized peptides of this example (i.e., 7-mer and its analogues) were listed below in Table 1.

TABLE 1

The present synthetic peptides

| Peptide Name. | Amino Acid Sequence | SEQ ID NO |
|---|---|---|
| 7-mer | $NH_2$-Asp-Leu-Tyr-Arg-Val-Arg-Ser-COOH<br>DLYRVRS | 2 |
| 7-mer analogues created by "D-amino acid substitution" | | |
| 7-mer DD | $NH_2$-(D-Asp)-Leu-Tyr-Arg-Val-Arg-Ser-COOH<br>DLYRVRS | 2 |
| 7-mer DL | $NH_2$-Asp-(D-Leu)-Tyr-Arg-Val-Arg-Ser-COOH<br>DLYRVRS | 2 |
| 7-mer DY | $NH_2$-Asp-Leu-(D-Tyr)-Arg-Val-Arg-Ser-COOH<br>DLYRVRS | 2 |
| 7-mer DR | $NH_2$-Asp-Leu-Tyr-(D-Arg)-Val-Arg-Ser-COOH<br>DLYRVRS | 2 |
| 7-mer DV | $NH_2$-Asp-Leu-Tyr-Arg-(D-Val)-Arg-Ser-COOH<br>DLYRVRS | 2 |
| 7-mer DR2 | $NH_2$-Asp-(D-Leu)-Tyr-Arg-Val-(D-Arg)-Ser-COOH<br>DLYRVRS | 2 |
| 7-mer DS | $NH_2$-Asp-Leu-Tyr-Arg-Val-Arg-(D-Ser)-COOH<br>DLYRVS | 2 |
| 7-mer analogues created by "alanine scanning" | | |
| 7-mer Da | $NH_2$-Ala-Leu-Tyr-Arg-Val-Arg-Ser-COOH<br>ALYRVRS | 3 |

TABLE 1-continued

The present synthetic peptides

| Peptide Name. | Amino Acid Sequence | SEQ ID NO |
|---|---|---|
| 7-mer La | NH$_2$-Asp-Ala-Tyr-Arg-Val-Arg-Ser-COOH<br>DAYRVRS | 4 |
| 7-mer Ya | NH$_2$-Asp-Leu-Ala-Arg-Val-Arg-Ser-COOH<br>DLARVRS | 5 |
| 7-mer Ra | NH$_2$-Asp-Leu-Tyr-Ala-Val-Arg-Ser-COOH<br>DLYAVRS | 6 |
| 7-mer Va | NH$_2$-Asp-Leu-Tyr-Arg-Ala-Arg-Ser-COOH<br>DLYRARS | 7 |
| 7-mer R2a | NH$_2$-Asp-Leu-Tyr-Arg-Val-Ala-Ser-COOH<br>DLYRVAS | 8 |
| 7-mer Sa | NH$_2$-Asp-Leu-Tyr-Arg-Val-Arg-Ala-COOH<br>DLYRVRA | 9 |

7-mer analogues created by "site specific replacement"

| Peptide Name. | Amino Acid Sequence | SEQ ID NO |
|---|---|---|
| 7-mer MK | NH$_2$-Asp-Leu-Tyr-Arg-Met-Lys-Ser-COOH<br>DLYRMKS | 10 |
| 7-mer KP | NH$_2$-Asp-Leu-Tyr-Lys-Val-Pro-Ser-COOH<br>DLYKVPS | 11 |
| 7-mer WI | NH$_2$-Asp-Leu-Trp-Arg-Ile-Arg-Ser-COOH<br>DLWRIRS | 12 |
| 7-mer IP | NH$_2$-Asp-Ile-Tyr-Arg-Val-Pro-Ser-COOH<br>DIYRVPS | 13 |
| 7-mer NV | NH$_2$-Asn-Val-Tyr-Arg-Val-Arg-Ser-COOH<br>NVYRVRS | 14 |
| 7-mer QK | NH$_2$-Asp-Leu-Tyr-Arg-Gln-Lys-Ser-COOH<br>DLYRQKS | 15 |
| 7-mer VFT | NH$_2$-Asp-Val-Phe-Arg-Val-Arg-Thr-COOH<br>DVFRVRT | 16 |
| 7-mer (V→L) | NH$_2$-Asp-Leu-Tyr-Arg-Leu-Arg-Ser-COOH<br>DLYRLRS | 17 |
| 7-mer (R2→Q) | NH$_2$-Asp-Leu-Tyr-Arg-Val-Gln-Ser-COOH<br>DLYRVQS | 18 |
| 7-mer (D→V) | NH$_2$-Val-Leu-Tyr-Arg-Val-Arg-Ser-COOH<br>VLYRVRS | 19 |
| 7-mer (D→F) | NH$_2$-Phe-Leu-Tyr-Arg-Val-Arg-Ser-COOH<br>FLYRVRS | 20 |
| 7-mer (D→L) | NH$_2$-Leu-Leu-Tyr-Arg-Val-Arg-Ser-COOH<br>LLYRVRS | 21 |
| Control Peptide (6-mer) | NH$_2$-Asp-Leu-Tyr-Arg-Val-Arg-COOH<br>DLYRVR | 22 |

The bold letter in any sequence indicates that particular amino acid is in D-form.

The effects of these synthesized peptides on the viability of the Raw284.7 macrophages were determined by MTT assay. Results are summarized in Table 2.

As evidenced in Table 2, 7-mer decreased the viability of Raw284.7 cells (55.7±4.24 versus 100±0.60, the control untreated cells). The 7-mer analogues created by alanine substitution at positions 1 and 2 of the 7-mer (i.e., 7-mer Da and 7-mer La) could sustain the inhibitory activity of 7-mer peptide. In contrast, alanine substitution for the 7-mer residues at positions 3, 4, 5, 6, and 7 resulted in the loss of the activity, which suggested the side chains in these residues were essential for the bioactivity of the 7-mer. The results also indicate that both substitutions at positions 1 (alanine for aspartate) and 2 (alanine for leucine) have relatively mild effect on the bioactivity of the 7-mer peptide, and the main chain flexibility of positions 1 and 2 may provide sites for 7-mer modification.

TABLE 2

Effect of alanine containing 7-mer peptides
on the viability of Raw264.7 macrophage cells

| Treatment | Raw264.7 cell viability | Treatment | Raw264.7 cell viability |
|---|---|---|---|
| untreated | 100 ± 0.60 | 7-mer Ra | 99.5 ± 1.51 |
| 7-mer | 55.7 ± 4.24* | 7-mer Va | 97.7 ± 0.60 |
| 7-mer Da | 52.9 ± 0.84* | 7-mer R2a | 94.6 ± 1.65 |
| 7-mer La | 57.4 ± 1.71* | 7-mer Sa | 93.1 ± 2.47 |
| 7-mer Ya | 97.6 ± 0.56 | | |

The concentration of the present synthetic peptide was 20 μM.
Data are expressed as mean + S.E. of 2 experiments carried out in duplicate.
*$p < 0.05$ vs. untreated cells.

Natural L-amino acids are the metabolically labile amino acids susceptible to cleavage by peptidase. Accordingly, the 7-mer analogues in which the natural L-form amino acids were replaced by their D-form counterparts were created. It was found that D-form amino acid substitution at positions 2, 3, 4, 6, and 7 caused loss of the inhibitory activity (Table 3). Only D-amino acid substitutions made to the 7-mer residues at positions 1 (D-aspartic acid for L-aspartic acid) and 5 (D-valine for L-valine) still possessed the inhibitor activity of 7-mer.

TABLE 3

Effect of 7-mer D-form analogues on the
viability of Raw264.7 macrophage cells

| Treatment | Rar264.7 cell viability | Treatment | Rar264.7 cell viability |
|---|---|---|---|
| untreated | 100 ± 1.82 | 7-mer DR | 100.3 ± 2.58 |
| 7-mer | 55.0 ± 3.66* | 7-mer DV | 57.9 ± 6.20* |
| 7-mer DD | 52.1 ± 1.45* | 7-mer DR2 | 102.9 ± 2.51 |
| 7-mer DL | 100.6 ± 1.48 | 7-mer DS | 107.2 ± 2.23 |
| 7-mer DY | 107.5 ± 0.63 | | |

The concentration of the present synthetic peptide was 20 μM.
Data are expressed as mean + S.E. of 2 experiments carried out in duplicate.
*$p < 0.05$ vs. untreated cells.

To further investigate the main chain flexibility in 7-mer, site specific amino acid substitutions in 7-mer were performed and the results are summarized in Table 4. The results indicated that each of the 7-mer analogues created by site specific replacements, which included 7-mer QK, 7-mer MK, 7-mer KP, 7-mer WI, 7-mer IP, 7-mer NV, 7-mer VFT, 7-mer (V→L), 7-mer (R2→Q), 7-mer (D→N), 7-mer (D→F), and 7-mer (D→L), could sustain 7-mer bioactivity, only partly.

TABLE 4

Effect of 7-mer analogues on the viability
of Raw264.7 macrophage cells

| Treatment | Raw264.7 cell viability | Treatment | Raw264.7 cell viability |
|---|---|---|---|
| untreated | 100 ± 1.81 | 7-mer QK | 77.7 ± 3.02* |
| 7-mer | 55.0 ± 3.66* | 7-mer VFT | 71.1 ± 2.48* |
| 7-mer MK | 81.4 ± 0.64* | 7-mer (V→L) | 61.1 ± 3.96* |
| 7-mer KP | 81.2 ± 3.43* | 7-mer (R2→Q) | 68.4 ± 1.25* |
| 7-mer WI | 77.9 ± 2.87* | 7-mer (D→V) | 56.8 ± 3.53* |
| 7-mer IP | 81.7 ± 4.50* | 7-mer (D→F) | 61.9 ± 4.91* |
| 7-mer NV | 74.8 ± 1.73* | 7-mer (D→L) | 57.6 ± 2.65* |

The concentration of the present synthetic peptide was 20 μM.
Data are expressed as mean + S.E. of 2 experiments carried out in duplicate.
*$p < 0.05$ vs. untreated cells Taken together, the results of this example indicated that the amino acid residues at positions 1 and 2 of the 7-mer are not critical in terms of its inhibitory activity; and the amino acid residues at positions 1 and 5 of the 7-mer can be either in L-form or in D-form, whereas the rest of the amino acid residues (i.e., residues at positions 2, 3, 4, 6, and 7 of the 7-mer) must remain in their nature forms (i.e., L-forms).

Example 2 The Present Synthetic Peptide Ameliorates IMQ-Induced Psoriasis-Like Skin Inflammation In this example, the efficacy of the present synthetic peptides of Example 1 on IMQ-induced psoriasis-like skin inflammation was investigated. To this purpose, animals (8-week-old mice) were given a daily topical dose of IMQ cream on the shaved back for six consecutive days, so as to induce psoriasis-like skin inflammation and desquamation (FIG. 1; left panel). The level of skin inflammation and desquamation reduced significantly when topical cream containing both IMQ and 7-mer peptide (100 μM) was applied (FIG. 1; middle panel). In addition, topical treatment with a reference compound Clobetasol (0.02%; an extremely potent synthetic glucocorticoid) also ameliorated desquamation formation (FIG. 1; right panel). However, contrast to the effect of 7-mer, Clobetasol caused skin atrophy throughout the entire back of the test animals.

Psoriasis is a disease resulted from abnormal keratinocyte proliferation, thus the effects of the present synthetic peptides on the proliferation of keratinocytes were also monitored in accordance with procedures described in the section of "Materials and Methods". Results are illustrated in FIG. 2.

Figure 2:
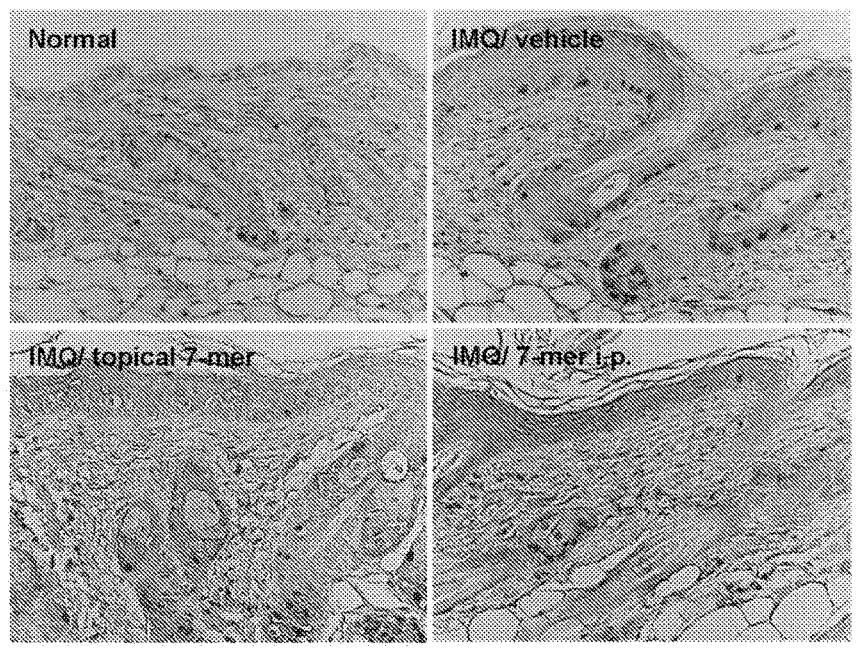
FIG. 2 illustrates the effect of 7-mer on IMQ-induced psorisasis-like epidermal hyperplasia, in which (A) are photographs depicting the effect of 7-mer on keratinocyte proliferation determined by BrdU incorporation, and (B) is a bar graph representing the mean number of BrdU positive cells±S.D. in four representative high power filed (HPF) in individual mice treated with IMQ in accordance with one embodiment of the present disclosure.
Figure 2:
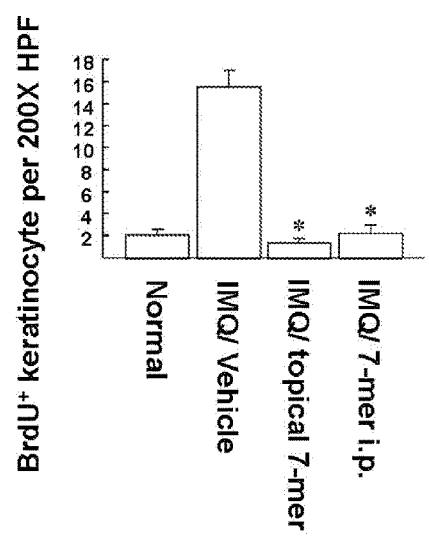

The photographs in FIG. 2 (panel A) show that significant amounts of BrdU were incorporated into the tissues after IMQ treatment, an indication of high level cell proliferation. By contrast, the 7-mer treated skins, either topically or via intraperitoneal injection, the number of BrdU-positive keratinocytes was significantly reduced (FIG. 2, panel B).

Taken together, the results in the present study confirm that the 7-mer peptides may ameliorate psoriasis-like skin inflammation.

Example 3 the Present Synthetic Peptide Ameliorates HOCl-Induced Skin Fibrosis Systemic sclerosis (SSc) is a connective tissue disorder characterized by skin and visceral fibrosis, microvascular damage, and autoimmunity. HOCl-induced mouse SSc is a murine model that mimics the main features of the human disease, especially the activation and hyperproliferation rate of skin fibroblasts. In this example, the efficacy of the present synthetic peptide on skin fibrosis was investigated by use of the HOCl-induced mouse SSc murine model in accordance with procedures described in the section of "Materials and Methods." Results are depicted in FIG. 3.

Figure 3:
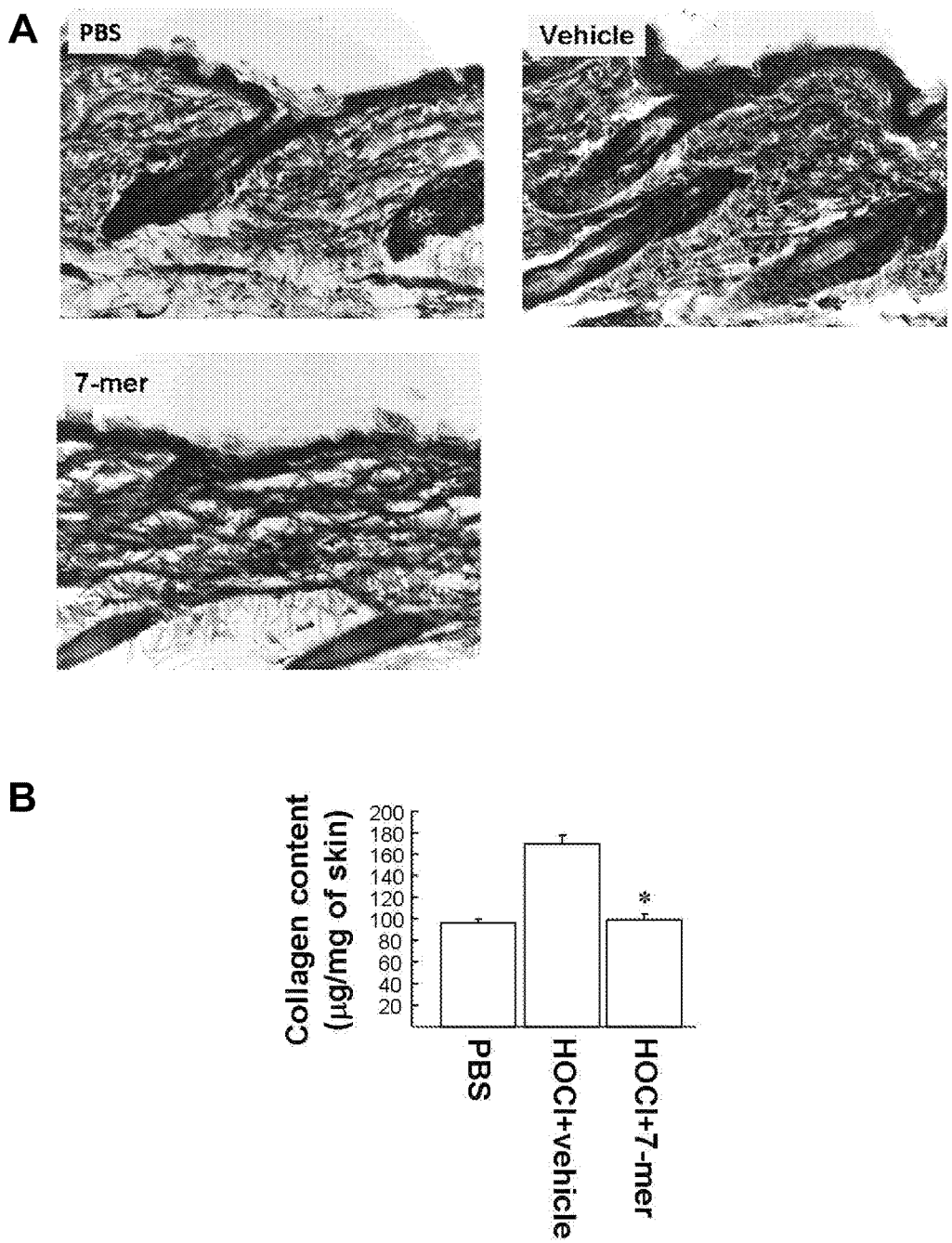
FIG. 3 illustrates the effect of the 7-mer on HOCl-induced skin fibrosis in accordance with one embodiment of the present disclosure, in which (A) are photographs of tissue section stained with Masson's trichrome to highlight the collage fibres at 6-weeks post HOCl injection, magnification is 200×; and (B) is a bar graph depicting the total collagen content in skins treated with vehicle, HOCl and HOCl/7-mer, respectively, *P<0.05 versus HOCl/vehicle treatment.

As depicted in the photographs of FIG. 3 (panel A), SSc mouse (i.e., mouse injected with HOCl/vehicle) displayed abnormal denser collagen matrix and more closely packed collagen fiber in the dermis, as compared with the PBS-treated mouse. Further, SSc mouse treated with the 7-mer displayed a significant decrease in the level of dermal collage, as compared with the un-treated SSC mouse (i.e., HOCl/vehicle-treated mouse), a level similar to that of the control, untreated mouse.

These results were corroborated by the measurement of the concentration of acid- and pepsin-soluble collagen content per milligram of normal skin or skins directly exposed to HOCl. The skin of SSC mice displayed a high level of collagen (μg collagen/mg skin), which was significantly reduced after the treatment of 7-mer peptide (FIG. 3, panel B, 169.9±7.75 for HOCl-treated SSC mice, 99.0±5.43 for 7-mer treated SSc mice).

Example 4 The Present Synthetic Peptide Prevents Lipopolysaccharide (LPS)-Induced Arthritis Rheumatoid arthritis (RA) is a chronic inflammatory disease characterized by an inflammation of the synovium leading to the destruction of joint cartilage and eventually the destruction of joint function. To this purpose, arthritis knees were created by injecting Sprague-Dawley rats with 25 μl of 2% hyaluronic acid (vehicle) containing LPS (2 or 10 μg) in the knees; whereas animals in the test group were injected with LPS and 7-mer (1 mM). Three days after the injection, synovial tissues were surgically removed, fixed, and stained with hematoxylin and eosin for histological analysis. Results are depicted in FIG. 4.

Figure 4:
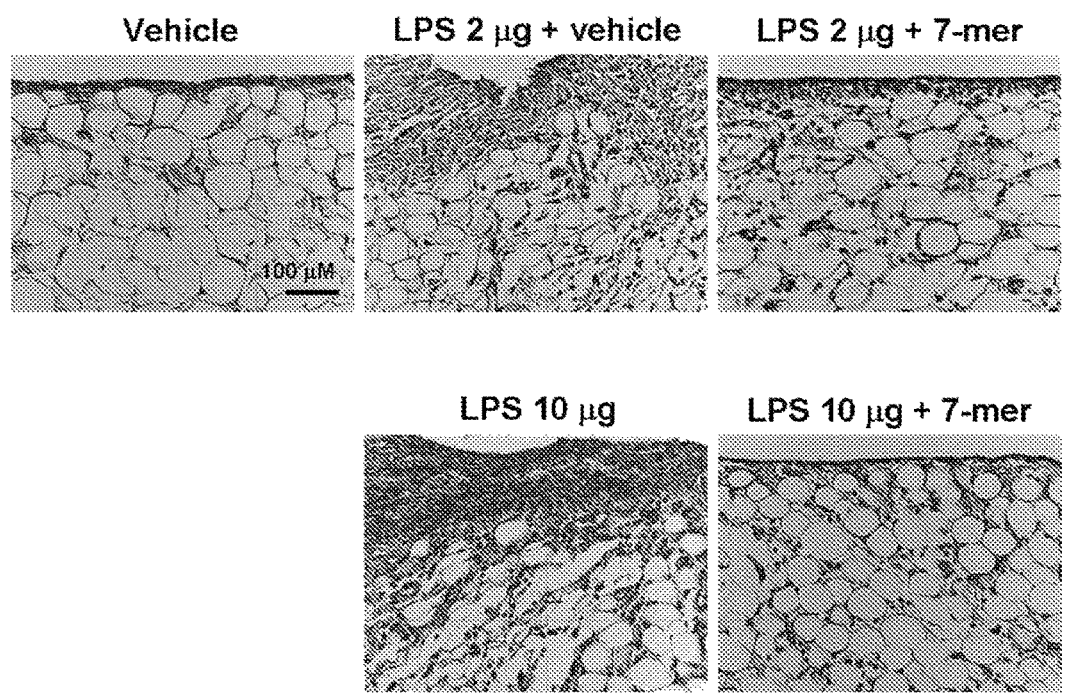
FIG. 4 are photographs depicting the effects of the present synthetic peptide on LPS-induced arthritis in accordance with one embodiment of the present disclosure.

As showed in the photographs of FIG. 4, the control animal (i.e., 2% HA vehicle injection) exhibited no leukocyte infiltration, an indication of no inflammation. By contrast, the photograph taken 3 days after LPS injection showed accumulation of proliferating synoviocytes and infiltrating leukocytes in synovium, a clear indication of prominent inflammation in the knee; this inflammation was significantly attenuated if the present 7-mer peptide was administered along with LPS.

Taking together, the finding in this example suggests that the present synthetic peptide may prevent inflammation from occurring in arthritic animals.

Example 5 The Present Synthetic Peptide Prevents the Development of Allergic Conjunctivitis (AC)

Allergic conjunctivitis (AC) is characterized by conjunctival eosinophilic infiltration. In this example, we investigate the anti-allergic effect of the present synthetic peptide by monitoring the immune response to ovalbumin (OVA) allergen in a murine AC model, which was established in accordance with the procedures described in the section of "Materials and Methods," and as depicted in panel A of FIG. 5.

Figure 5:
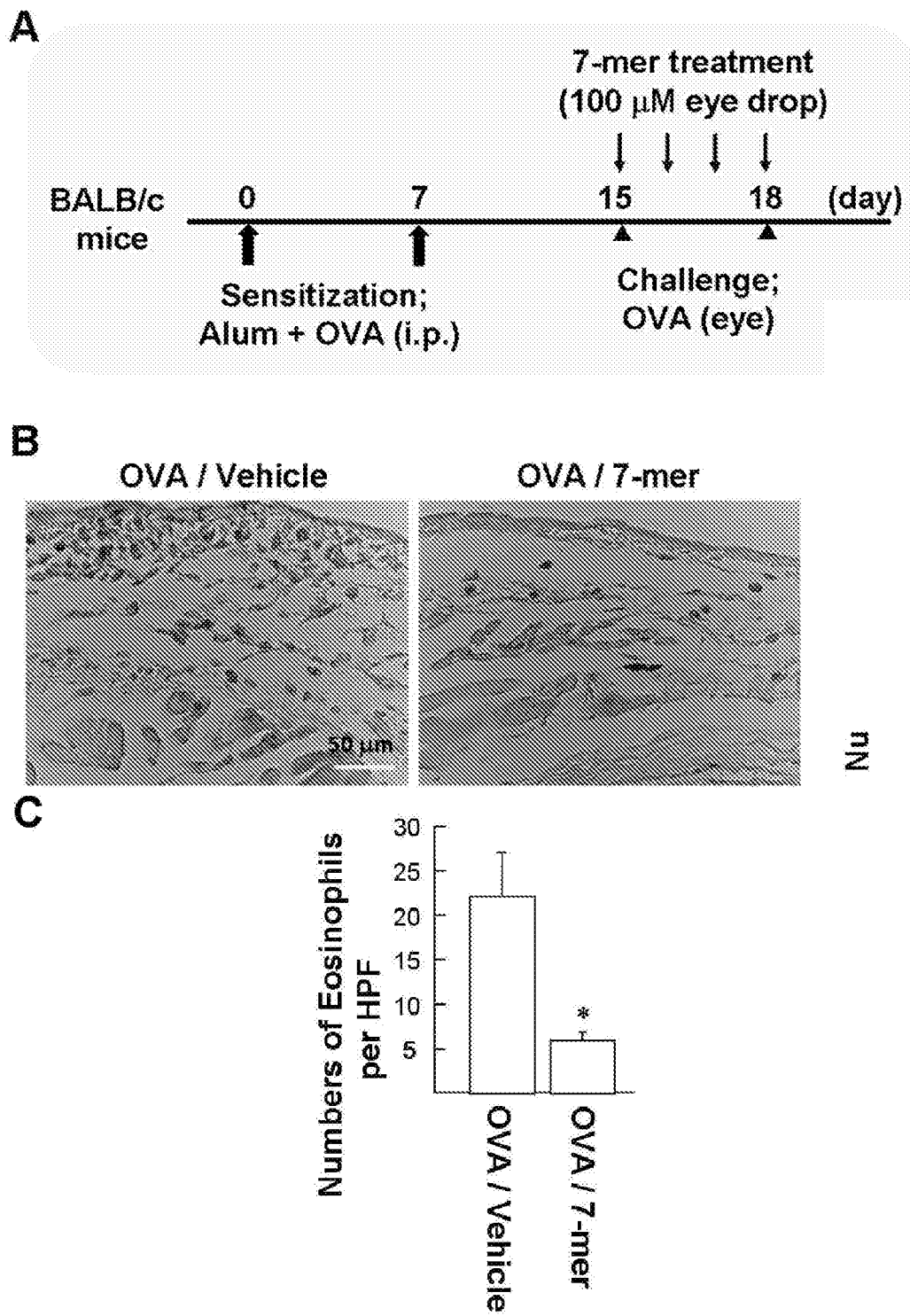
FIG. 5 are photographs illustrating the effects of 7-mer peptide on is OVA-induced allergic conjunctivitis (AC) in accordance with one embodiment of the present disclosure, in which (A) is the protocol for establishing the experimental AC model, (B) are histological staining photographs, and (C) is a bar graph depicting the numbers of eosinophils in AC mice treated with or without the 7-mer, *P<0.05 versus OVA-challenged.

Histological analysis revealed significant infiltration of eosinophils in the conjunctiva of OVA challenged mice after systemic priming and local boosting with OVA (FIG. 5, panel B). However, the infiltration of eosinophils in the conjunctiva decreased significantly in mice treated with 7-mer (FIG. 5, panel C). The result suggests that 7-mer may suppress eosinophilic infiltration in OVA-induced allergic model.

Example 6 The Present Synthetic Peptide Prevents the Development of Allergic Asthma In this example, we investigate the efficacy of the present synthetic peptide on allergic asthma by use of the well-characterized murine model of allergic airway disease, employing ovalbumin as the antigen. The experimental murine asthma model was established in accordance with the procedures described in the section of "Materials and Methods," and as depicted in panel A of FIG. 6.

Figure 6:
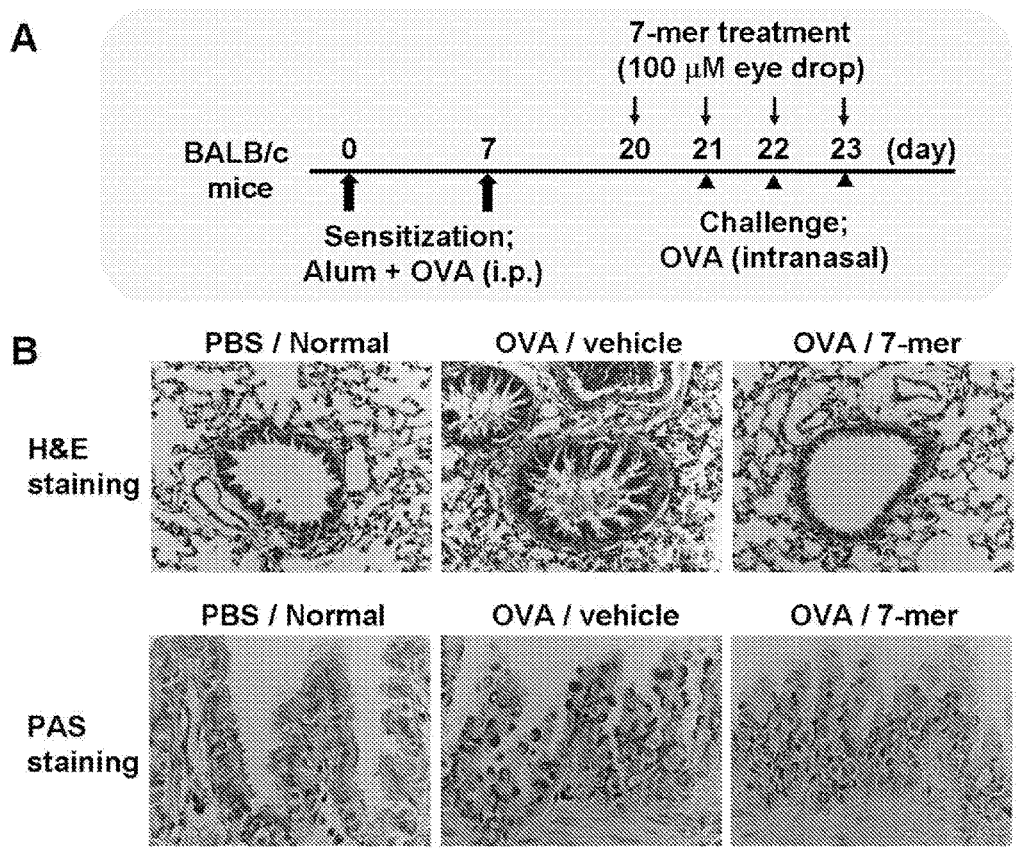
FIG. 6 illustrates the effects of the 7-mer peptide on the development of allergic asthma in accordance with one embodiment of the present disclosure, in which (A) is the protocol for establishing the experimental allergic asthma model, (B) are histological staining photographs respectively stained by hematoxylin and eosin (H&E), and PAS.

Histopathological studies by H&E staining demonstrated that OVA challenged mice exhibited leukocyte infiltration around peribronchial and perivascular spaces (FIG. 6, panel B, H&E staining). The majority of the infiltrated inflammatory cells were macrophages and eosinophils. However, the inflammatory cell infiltration was significantly reduced in 7-mer treated mice, as compared to OVA challenged mice. In addition, mucus overproduction caused by goblet cell hyperplasia is characteristic of airway obstruction and airway remodeling. The mucus secretion was markedly reduced in 7-mer-treated mice, as compared to OVA challenged mice (FIG. 6, panel B, PAS staining).

The result suggests that 7-mer may suppress the development of OVA-induced allergic pulmonary inflammation.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of prophylactically treating or palliative treating a subject suffering from asthma comprising administering to the subject an effective amount of a synthetic peptide consisting of 7 consecutive amino acid residues set forth as $X_1X_2X_3X_4X_5X_6X_7$ (SEQ ID NO: 1), wherein,
   $X_1$ is alanine (A), aspartic acid (D), asparagine (N), leucine (L), phenylalanine (F), or valine (V);
   $X_2$ is alanine (A), isoleucine (I), leucine (L), or valine (V);
   $X_3$ is phenylalanine (F), tyrosine (Y) or tryptophan (W);
   $X_4$ is arginine (R) or lysine (K);
   $X_5$ is valine (V), methionine (M), isoleucine (I), leucine (L), or glutamine (Q);
   $X_6$ is arginine (R), glutamine (Q), lysine (K) or proline (P);
   $X_7$ is serine (S) or threonine (T); and
   each $X_2$, $X_3$, $X_4$, $X_6$ and $X_7$ are independently L-form amino acid residues; and
   the synthetic peptide has the amino acid sequence that is any of SEQ ID NOs: 2, 3, 4, 10, 11, 12, 13, 14, 15, 16, 17, 18, 19, 20, or 21.

2. The method of claim 1, wherein at least one of $X_1$ and $X_5$ is a D-form amino acid residue.

3. The method of claim 2, wherein the synthetic peptide has the amino acid sequence of SEQ ID NO: 2.

4. The method of claim 3, wherein $X_1$ is in D-form.

5. The method of claim 3, wherein $X_5$ is in D-form.

6. The method of claim 1, wherein the subject is a human.

7. The method of claim 1, further comprising administered to the subject an effective amount of an anti-inflammatory agent.

8. The method of claim 7, wherein the anti-inflammatory agent is a non-steroid anti-inflammatory drug (NSAID).

* * * * *